US009771355B2

(12) United States Patent
Kandula

(10) Patent No.: US 9,771,355 B2
(45) Date of Patent: Sep. 26, 2017

(54) COMPOSITIONS AND METHODS FOR THE TREATMENT OF EPILEPSY AND NEUROLOGICAL DISORDERS

(71) Applicant: Mahesh Kandula, Andhra Pradesh (IN)

(72) Inventor: Mahesh Kandula, Andhra Pradesh (IN)

(73) Assignee: CELLIX BIO PRIVATE LIMITED, Hyderabad, Telangana (IN)

( * ) Notice: Subject to any disclaimer, the term of this patent is extended or adjusted under 35 U.S.C. 154(b) by 0 days.

(21) Appl. No.: 14/626,931

(22) Filed: Feb. 20, 2015

(65) Prior Publication Data

US 2016/0090379 A1 Mar. 31, 2016

(51) Int. Cl.
| | | |
|---|---|---|
| *A61K 31/55* | (2006.01) | |
| *C07D 223/28* | (2006.01) | |
| *C07D 401/12* | (2006.01) | |
| *C07D 403/12* | (2006.01) | |
| *C07D 405/12* | (2006.01) | |
| *C07D 409/12* | (2006.01) | |
| *C07D 495/02* | (2006.01) | |

(52) U.S. Cl.
CPC ......... *C07D 409/12* (2013.01); *C07D 223/28* (2013.01)

(58) Field of Classification Search
CPC .... A61K 31/55; C07D 223/28; C07D 401/12; C07D 403/12; C07D 405/12; C07D 409/12; C07D 495/02
USPC .......................................... 514/217; 540/589
See application file for complete search history.

(56) References Cited

U.S. PATENT DOCUMENTS

| | | | |
|---|---|---|---|
| 2,807,644 A | 9/1957 | Moore et al. | |
| 4,011,342 A | 3/1977 | Schwartz et al. | |
| 4,404,366 A | 9/1983 | Boguslaski et al. | |
| 4,412,992 A | 11/1983 | Chan | |
| 4,440,763 A | 4/1984 | Lover | |
| 4,550,109 A | 10/1985 | Folkers et al. | |
| 4,564,628 A | 1/1986 | Horn | |
| 4,778,794 A | 10/1988 | Naruse et al. | |
| 4,873,259 A | 10/1989 | Summers, Jr. et al. | |
| 4,920,122 A | 4/1990 | Naruse et al. | |
| 4,963,590 A | 10/1990 | Backstrom et al. | |
| 5,013,727 A | 5/1991 | Halskov | |
| 5,102,870 A | 4/1992 | Florine et al. | |
| 5,104,887 A | 4/1992 | Schoenwald et al. | |
| 5,120,738 A | 6/1992 | Ikawa et al. | |
| 5,242,937 A | 9/1993 | Pierce, Jr. | |
| 5,352,703 A | 10/1994 | Quadro | |
| 5,719,168 A | 2/1998 | Laurent | |
| 5,830,907 A | 11/1998 | Doble et al. | |
| 5,886,001 A | 3/1999 | Schmidhammer | |
| 6,156,777 A | 12/2000 | Hall et al. | |
| 6,296,873 B1 * | 10/2001 | Katzhendler | A61K 9/2031 424/464 |
| 6,414,008 B1 | 7/2002 | Hauel et al. | |
| 6,602,915 B2 | 8/2003 | Uhrich | |
| 6,610,708 B1 | 8/2003 | Asai et al. | |
| 6,613,802 B1 | 9/2003 | Luskey et al. | |
| 7,101,912 B2 | 9/2006 | Xiang et al. | |
| 7,544,834 B2 | 6/2009 | Sumikawa et al. | |
| 7,645,767 B2 | 1/2010 | Singh et al. | |
| 7,910,568 B2 | 3/2011 | Wallace et al. | |
| 8,025,897 B2 | 9/2011 | Bunick et al. | |
| 8,778,991 B2 | 7/2014 | Gangakhedkar et al. | |
| 8,952,068 B2 | 2/2015 | Kandula | |
| 2002/0049155 A1 | 4/2002 | Hogenkamp | |
| 2003/0139437 A1 | 7/2003 | Dobrozsi et al. | |
| 2003/0220468 A1 | 11/2003 | Lai et al. | |
| 2003/0232867 A1 | 12/2003 | Kobayashi et al. | |
| 2004/0010038 A1 | 1/2004 | Blaugrund et al. | |
| 2004/0048924 A1 | 3/2004 | Bunick et al. | |
| 2004/0106576 A1 | 6/2004 | Jerussi et al. | |
| 2004/0170680 A1 | 9/2004 | Oshlack et al. | |
| 2004/0215004 A1 | 10/2004 | Berkner et al. | |
| 2004/0259953 A1 | 12/2004 | Deregnaucourt et al. | |
| 2005/0014799 A1 | 1/2005 | Degenhardt et al. | |
| 2005/0020665 A1 | 1/2005 | Neu | |
| 2005/0106248 A1 | 5/2005 | Dixit et al. | |

(Continued)

FOREIGN PATENT DOCUMENTS

| | | | |
|---|---|---|---|
| AU | 514991 B2 | 3/1981 | |
| CA | 1199916 A1 | 1/1986 | |

(Continued)

OTHER PUBLICATIONS

"Amidines and related compounds. 6. Studies on structure-activity relationships of antihypertensive and antisecretory agents related to clonidine", US National Library of Medicine National Institutes of HealthSearch database, Jan. 1975, by Jen T et al. (p. 1) http://www.ncbi.nlm.nih.gov/pubmed/234014?report=abstract.

"Progress Application of Fumaric Acid and the Derivatives of Fumaric Acid,Guangdong Chemical Industry", Guangdong Chemical Industry, Jul. 31, 2007, by Gao Cuiying1 et al. (p. 1) http://en.cnki.com.cn/Article_en/CJFDTOTAL-GDHG200707027.htm.

"1H and 13C Nuclear Magnetic Resonance Studies on the Tautomerism, Geometrical Isomerism and Conformation of some Cyclic Amidines, Guanidines and Related Systems", Journal of American Chemical Society, May 1975, by Lloyd M. Jackman et al. (p. 1) http://pubs.acs.org/doi/pdf/10.1021/ja00843a033.

(Continued)

*Primary Examiner* — Brenda Coleman
(74) *Attorney, Agent, or Firm* — Raj Abhyanker, P.C.

(57) ABSTRACT

The invention relates to the compounds of formula I and formula Ia or its pharmaceutical acceptable polymorphs, solvates, enantiomers, stereoisomers and hydrates thereof. The pharmaceutical compositions comprising an effective amount of formula I or formula Ia; and methods for treating or preventing epilepsy, seizures and convulsions may be formulated for oral, buccal, rectal, topical, transdermal, transmucosal, intravenous, parenteral administration, syrup, or injection. Such compositions may be used to treatment of epilepsy, seizures and convulsions.

6 Claims, 2 Drawing Sheets

(56) References Cited

U.S. PATENT DOCUMENTS

| | | |
|---|---|---|
| 2005/0208129 A1 | 9/2005 | Aiache et al. |
| 2005/0244486 A1 | 11/2005 | Caldwell et al. |
| 2006/0014837 A1 | 1/2006 | Deregnaucourt et al. |
| 2006/0057644 A1 | 3/2006 | Kelly et al. |
| 2006/0058373 A1 | 3/2006 | Abdel-Magid et al. |
| 2006/0142566 A1 | 6/2006 | Mathes et al. |
| 2006/0270635 A1 | 11/2006 | Wallace et al. |
| 2006/0270706 A1 | 11/2006 | Kimura et al. |
| 2007/0259930 A1 | 11/2007 | Bozik et al. |
| 2008/0020996 A1 | 1/2008 | Singh et al. |
| 2008/0058362 A1 | 3/2008 | Singh et al. |
| 2008/0064743 A1 | 3/2008 | Shah et al. |
| 2008/0132578 A1 | 6/2008 | Jerussi et al. |
| 2008/0207564 A1 | 8/2008 | Wallace et al. |
| 2008/0221111 A1 | 9/2008 | Hesslinger et al. |
| 2008/0227985 A1 | 9/2008 | Raje et al. |
| 2008/0262053 A1 | 10/2008 | Reess |
| 2008/0269166 A2 | 10/2008 | Jerussi et al. |
| 2008/0280936 A1 | 11/2008 | Tung |
| 2008/0319222 A1 | 12/2008 | Sutton |
| 2009/0075942 A1 | 3/2009 | Czarnik |
| 2009/0118365 A1 | 5/2009 | Benson, III et al. |
| 2009/0131535 A1 | 5/2009 | Blaugrund et al. |
| 2009/0326062 A1 | 12/2009 | Palomo Nicolau et al. |
| 2010/0004255 A1 | 1/2010 | Belardinelli et al. |
| 2010/0016328 A1 | 1/2010 | Kakkis et al. |
| 2010/0081713 A1 | 4/2010 | Sharma et al. |
| 2010/0316712 A1 | 12/2010 | Nangia et al. |
| 2011/0021628 A1 | 1/2011 | Estrada et al. |
| 2011/0087028 A1 | 4/2011 | Hwang et al. |
| 2011/0165234 A1 | 7/2011 | Dixit et al. |
| 2011/0172240 A1 | 7/2011 | Milne et al. |
| 2011/0218180 A1 | 9/2011 | Singh et al. |
| 2011/0229561 A1 | 9/2011 | Kapoor et al. |
| 2011/0230514 A1 | 9/2011 | Tung |
| 2011/0288140 A1 | 11/2011 | Attali et al. |
| 2011/0300190 A1 | 12/2011 | Kandula |
| 2011/0313036 A1 | 12/2011 | Estrada et al. |
| 2011/0313176 A1 | 12/2011 | Khunt et al. |
| 2012/0021046 A1 | 1/2012 | Capomacchia et al. |
| 2012/0022072 A1 | 1/2012 | Kakkis et al. |
| 2012/0046272 A1 | 2/2012 | Sesha |
| 2012/0093922 A1 | 4/2012 | Manku et al. |
| 2012/0095003 A1 | 4/2012 | Gangakhedkar et al. |
| 2012/0115817 A1 | 5/2012 | Dos Santos et al. |
| 2012/0157523 A1 | 6/2012 | Gangakhedkar et al. |
| 2012/0208850 A1 | 8/2012 | Kong et al. |
| 2012/0302794 A1 | 11/2012 | Jerussi et al. |
| 2013/0065909 A1 | 3/2013 | Milne et al. |
| 2013/0190327 A1 | 7/2013 | Milne et al. |
| 2013/0217737 A1 | 8/2013 | Hasse et al. |
| 2013/0267605 A1 | 10/2013 | Scheuring et al. |
| 2013/0274306 A1 | 10/2013 | Attali et al. |
| 2014/0080315 A1 | 3/2014 | Wilhelm-Ogunbiyi et al. |
| 2014/0100372 A1 | 4/2014 | Raje et al. |
| 2014/0134753 A1 | 5/2014 | Kelly et al. |
| 2014/0155455 A1 | 6/2014 | Osterloh et al. |
| 2014/0228389 A1 | 8/2014 | Shah et al. |
| 2014/0235710 A1 | 8/2014 | Estrada et al. |
| 2015/0148398 A1 | 5/2015 | Attali et al. |

FOREIGN PATENT DOCUMENTS

| | | |
|---|---|---|
| CN | 1224610 A | 8/1999 |
| CN | 1300213 A | 6/2001 |
| CN | 1672678 A | 9/2005 |
| CN | 1706813 A | 12/2005 |
| CN | 1248690 C | 4/2006 |
| CN | 1897935 A | 1/2007 |
| CN | 101023056 A | 8/2007 |
| CN | 101186583 A | 5/2008 |
| CN | 101202326 A | 6/2008 |
| CN | 101208326 A | 6/2008 |
| CN | 100448852 C | 1/2009 |
| CN | 101390854 A | 3/2009 |
| CN | 100548300 C | 10/2009 |
| CN | 101569618 A | 11/2009 |
| CN | 101717392 A | 6/2010 |
| CN | 101724934 A | 6/2010 |
| CN | 101921245 A | 12/2010 |
| CN | 102002053 A | 4/2011 |
| CN | 102123763 A | 7/2011 |
| CN | 102149673 A | 8/2011 |
| CN | 102336767 A | 2/2012 |
| CN | 102633799 A | 8/2012 |
| CN | 102050815 B | 4/2014 |
| EP | 0141393 A2 | 5/1985 |
| EP | 0150787 A2 | 8/1985 |
| EP | 0421441 A2 | 4/1991 |
| EP | 0934928 A1 | 8/1999 |
| EP | 1063230 A1 | 12/2000 |
| EP | 1695962 A1 | 8/2006 |
| EP | 1870395 A1 | 12/2007 |
| EP | 1889835 A1 | 2/2008 |
| EP | 1997493 A1 | 12/2008 |
| EP | 2298777 A2 | 3/2011 |
| EP | 2450039 A1 | 5/2012 |
| FR | 2722199 A1 | 1/1996 |
| GB | 1014020 A | 12/1965 |
| GB | 1356470 A | 6/1974 |
| GB | 2116541 A | 9/1983 |
| JP | 5412340 A | 1/1979 |
| JP | 56077259 A | 6/1981 |
| JP | S6089474 A | 5/1985 |
| RU | 2436772 C2 | 12/2011 |
| WO | 8500599 A1 | 2/1985 |
| WO | 9114430 A1 | 10/1991 |
| WO | 9118865 A1 | 12/1991 |
| WO | 9305029 A1 | 3/1993 |
| WO | 9413298 A1 | 6/1994 |
| WO | 9522546 A1 | 8/1995 |
| WO | 9531464 A1 | 11/1995 |
| WO | 9822433 A1 | 5/1998 |
| WO | 9852556 A1 | 11/1998 |
| WO | 0041693 A2 | 7/2000 |
| WO | 0059851 A1 | 10/2000 |
| WO | 0122967 A1 | 4/2001 |
| WO | 0200167 A2 | 1/2002 |
| WO | 0234713 A1 | 5/2002 |
| WO | 02062332 A1 | 8/2002 |
| WO | 02087512 A2 | 11/2002 |
| WO | 03018004 A2 | 3/2003 |
| WO | 03030877 A1 | 4/2003 |
| WO | 03086391 A1 | 10/2003 |
| WO | 03087038 A1 | 10/2003 |
| WO | 03097656 A2 | 11/2003 |
| WO | 2004031155 A1 | 4/2004 |
| WO | 2004052841 A1 | 6/2004 |
| WO | 2004075886 A1 | 9/2004 |
| WO | 2004078769 A1 | 9/2004 |
| WO | 2004082402 A1 | 9/2004 |
| WO | 2005046575 A2 | 5/2005 |
| WO | 2005110381 A1 | 11/2005 |
| WO | 2005116086 A2 | 12/2005 |
| WO | 2006075123 A1 | 7/2006 |
| WO | 2006096996 A1 | 9/2006 |
| WO | 2006120176 A2 | 11/2006 |
| WO | 2006125293 A1 | 11/2006 |
| WO | 2007086493 A1 | 8/2007 |
| WO | 2007121188 A2 | 10/2007 |
| WO | 2008030567 A2 | 3/2008 |
| WO | 2008074033 A1 | 6/2008 |
| WO | 2008079404 A2 | 7/2008 |
| WO | 2008089008 A2 | 7/2008 |
| WO | 2008098960 A1 | 8/2008 |
| WO | 2008113056 A2 | 9/2008 |
| WO | 2008137474 A1 | 11/2008 |
| WO | 2009002297 A1 | 12/2008 |
| WO | 2009056791 A1 | 5/2009 |
| WO | 2009061934 A1 | 5/2009 |
| WO | 2010020969 A1 | 2/2010 |
| WO | 2010031819 A1 | 3/2010 |
| WO | 2010115252 A1 | 10/2010 |
| WO | 2010127099 A2 | 11/2010 |

(56) References Cited

FOREIGN PATENT DOCUMENTS

| WO | 2010147666 A1 | 12/2010 |
|---|---|---|
| WO | 2011017800 A1 | 2/2011 |
| WO | 2011060945 A2 | 5/2011 |
| WO | 2011085211 A1 | 7/2011 |
| WO | 2011089216 A1 | 7/2011 |
| WO | 2011106688 A1 | 9/2011 |
| WO | 2011154833 A1 | 12/2011 |
| WO | 2012007352 A1 | 1/2012 |
| WO | 2012025213 A2 | 3/2012 |
| WO | 2012027543 A1 | 3/2012 |
| WO | 2012055567 A2 | 5/2012 |
| WO | 2012115695 A1 | 8/2012 |
| WO | 2013008182 A1 | 1/2013 |
| WO | 2013017974 A1 | 2/2013 |
| WO | 2013024376 A1 | 2/2013 |
| WO | 2013027150 A1 | 2/2013 |
| WO | 2013152608 A1 | 10/2013 |
| WO | 2013167988 A1 | 11/2013 |
| WO | 2013167993 A1 | 11/2013 |
| WO | 2013167996 A1 | 11/2013 |
| WO | 2013168022 A1 | 11/2013 |
| WO | 2013175377 A2 | 11/2013 |
| WO | 2014174425 A2 | 10/2014 |

OTHER PUBLICATIONS

"Enzyme-catalyzed regioselective synthesis of lipophilic guaifenesin ester derivatives", Journal of Molecular Catalysis B: Enzymatic, vol. 27, Issues 2-3, Feb. 2, 2004, pp. 97-102 by Na Wang et al. (p. 1) http://www.sciencedirect.com/science/article/pii/S1381117703002650.

"Interactions of the advanced glycation end product inhibitor pyridoxamine and the antioxidant α-lipoic acid on insulin resistance in the obese Zucker rat", Metabolism, vol. 57, Issue 10, Oct. 2008, pp. 1465-1472 by Elizabeth A. Muellenbach et al. (p. 1) http://www.sciencedirect.com/science/article/pii/S0026049508002047.

"Effect of pentoxifylline and/or alpha lipoic acid on experimentally induced acute pancreatitis.", European Journal of Pharmacology, Jun. 21, 2010 by Amany A. Abdin et al. (p. 1) http://www.ncbi.nlm.nih.gov/pubmed/20599924.

"Pretreatment with pentoxifylline and N-acetylcysteine in liver ischemia reperfusion-induced renal injury.", Renal Failure, Feb. 27, 2012, by Behjat Seifi et al. (p. 1) http://www.ncbi.nlm.nih.gov/pubmed/22364443.

Synthesis and evaluation of Ketorolac ester prodrugs for transdermal delivery,Journal of Pharmaceutical Science, by Hea-Jeong Doh et al. May 2003 (p. 1) http://onlinelibrary.wiley.com/doi/10.1002/jps.10353/abstract.

Probing the skin permeation of fish oil EPA and ketoprofen 1. NMR spectroscopy and molecular modelling, International Journal of Pharmaceutics, vol. 338, Issues 1-2, Jun. 29, 2007, pp. 207-212 by Christopher P. Thomas et al. (pp. 2) http://www.sciencedirect.com/science/article/pii/S0378517307001330.

RN 67195-24-8 Registry Entered STN: Nov. 16, 1984 (pp. 2) http://chem.sis.nlm.gov/chemidplus/rn/67195-24-8.

"Palladium-Catalyzed Direct Arylation of Benzoxazoles with Unactivated Simple Arenes", Electronic Supplementary Material (ESI) for Chemical Communications, Sep. 14, 2012, by Ge Wu et al. (pp. 84) http://www.rsc.org/suppdata/cc/c2/c2cc34238c/c2cc34238c.pdf.

"Tafamidis", from Nature Review Drug Discovery 11, Mar. 2012 by Gerard Said et al. (pp. 2) http://www.nature.com/nrd/journal/v11/n3/full/nrd3675.html.

"The role of structural information in the discovery of direct thrombin and factor Xa inhibitors", Trends in Pharmacological Sciences, vol. 33, Issue 5, Apr. 2012 (p. 1) http://www.cell.com/trends/pharmacological-sciences/abstract/S0165-6147(12)00036-3.

"Nicotinamide-substituted complexes as redox markers. 1. Synthesis and UV investigation of rhenium and technetium mixed-ligand systems", Journal of Labelled Compounds, Jan. 1998 by T. Kniess et al. (p. 1) http://www.researchgate.net/publication/243806712_Nicotinamide-substituted_complexes_as_redox_markers._1. Synthesis and UV investigation of rhenium and technetium mixed-ligand systems.

"Recent Advances in the Mechanism of Pyridoxine responsive Disorders", Journal of Inherited Metabolic Disorder, 1985 by B. Fowler et al. (pp. 8).

"Enantioseparation of anaesthetic drugs by capillary zone electrophoresis using cyclodextrin-containing background electrolytes", Electrophoresis, 19, 731-737, May 1998 by Ahmad Amini et al. (p. 7).

"Antioxidant and Radical Scavenging Properties of 8-Oxo Derivatives of Xanthine Drugs Pentoxifylline and Lisofyllin", Biochemical and Biophysical Research Communications, vol. 288, Issue 5, Nov. 16, 2001 by Vadiraja B. Bhat et al. (p. 1) http://www.sciencedirect.com/science/article/pii/S0006291X01959224.

"Biochemical and Biophysical Research Communications", Database CAPLUS on STN, Acc. No. 2009:265795, (2009), 380(3), pp. 586-590, by Yamada et al. (pp. 3).

"N-Acylcysteamines", CAPLUS 1959:121370 by Tozaburo Kurihara et al. (p. 1), 1959.

"Advances in Prodrug Design", Mini-Reviews in Medical Chemistry, 2005, 5 pp. 893-914 by Silva AT et al. (pp. 22).

"Drug Discovery Today", vol. 13, pp. 21-22 in Nov. 2008 by Stefan Schafer et al. (pp. 4).

"From bench to clinic and back", Perspective on the 1st IQPC Translation Research conference, Journal of Translational Medicine, Dec. 20, 2004 by Heidi Hoag et al. (pp. 8).

Synthesis of α4-N-acyl pyridoxamines and hydrolysis of α4-N-octanoyl pyridoxamine, Fac. Pharm. Sci., Mukogawa Women's University., Nishinomiya, Japan, in 1976, 50, 85-91 by Mizuno et al. (pp. 2).

"Cancer Treatment-Induced Mucositis Pain: Strategies for Assessment and Management", Therapeutics and Clinical Risk Management, vol. 2(3): 251-258, Sep. 2006 by Debra J Harris (pp. 8) http://www.ncbi.nlm.nih.gov/pmc/articles/PMC1936261/.

\* cited by examiner

COMPOSITIONS AND METHODS FOR THE TREATMENT OF EPILEPSY AND NEUROLOGICAL DISORDERS

CLAIM OF PRIORITY

This application is a national phase filing of the Patent Cooperation Treaty (PCT) application No. PCT/IN2015/000086 titled "COMPOSITIONS AND METHODS FOR THE TREATMENT OF EPILEPSY AND NEUROLOGICAL DISORDERS" filed on Feb. 13, 2015, which further claims priority to patent application Indian Patent Application No. 6399/CHE/2014, filed on Dec. 19, 2014, and Indian Patent Application No. 4739/CHE/2014 filed on Sep. 26, 2014. The entire disclosure of the priority applications are relied on for all purposes and is incorporated into this application by reference.

FIELD OF THE INVENTION

This disclosure generally relates to compounds and compositions for the treatment of epilepsy and neurological disorders. More particularly, this invention relates to treating subjects with a pharmaceutically acceptable dose of compounds, crystals, esters, salts, hydrates, prodrugs, or mixtures thereof.

BACKGROUND OF THE INVENTION

Disorders such as the periodic paralyses, nondystrophic myotonias, episodic ataxias, paroxysmal dyskinesias, long QT syndrome, migraine headache, and epilepsy all share the feature of being episodic in nature. Affected individuals are often completely healthy between attacks. Stress and fatigue precipitate attacks in all of these diseases, and various dietary factors can also contribute to attack onset. The drugs used to treat these disorders overlap significantly.

Carbonic anhydrase inhibitors are effective for many patients with periodic paralysis, episodic ataxia, and migraine headache. Mexiletine hydrochloride, an effective antiarrhythmic medication, can be beneficial in treating myotonia in patients with paramyotonia congenita. The anticonvulsant carbamazepine is an extremely efficacious drug for treating the episodic movements of paroxysmal kinesigenic dyskinesia. All of these disorders have a tendency to begin in infancy or childhood and to worsen through adolescence and young adult life. In some cases, they decrease in severity and frequency in middle to late adult life.

Epilepsy and stroke are the 2 most common epilepsy and neurological disorders: at any one time 7 in 1000 people in the general population have epilepsy. Epilepsy usually begins in childhood, potentially impeding education, employment, social relationships and development of a sense of self-worth. Prompt, accurate diagnosis with appropriate social and medical management will optimize the situation. A family physician, in conjunction with a neurologist, can ascertain (a) if the episodes represent epileptic seizures and (b) if so, which epileptic syndrome they represent.

A harmonized partnership between family physician and neurologist will facilitate the recognition and care of epileptic disorders. As the role of the family physician in the care of patients with epilepsy increases, the principles delineated in this article will be ever more utilized. Trigeminal neuralgia is defined as sudden, usually unilateral, severe, brief, stabbing recurrent episodes of pain within the distribution of one or more branches of the trigeminal nerve, which has a profound effect on quality of life. The diagnosis is made on history alone, and time needs to be taken to elicit the key features and differentiate from toothache or one of the trigeminal autonomic cephalalgias. Most trigeminal neuralgia is idiopathic, but a small percentage is due to secondary causes for example, tumours or multiple sclerosis which can be picked up on CT or MRI.

Recently published international guidelines suggest that carbamazepine and oxcarbazepine are the first-line drugs. There is limited evidence for the use of lamotrigine and baclofen. If there is a decrease in efficacy or tolerability of medication, surgery needs to be considered.

Managing acute pathology of often relies on the addressing underlying pathology and symptoms of the disease. There is currently a need in the art for new compositions to treatment of Epilepsy and neurological disorders.

SUMMARY OF THE INVENTION

The present invention provides compounds, compositions containing these compounds and methods for using the same to treat, prevent and/or ameliorate the effects of the conditions such as Epilepsy and neurological disorders.

The invention herein provides compositions comprising of formula I or pharmaceutical acceptable salts thereof. The invention also provides pharmaceutical compositions comprising one or more compounds of formula I or enantiomers of formula I or intermediates thereof and one or more of pharmaceutically acceptable carriers, vehicles or diluents. These compositions may be used in the treatment of Epilepsy and neurological disorders and its associated complications.

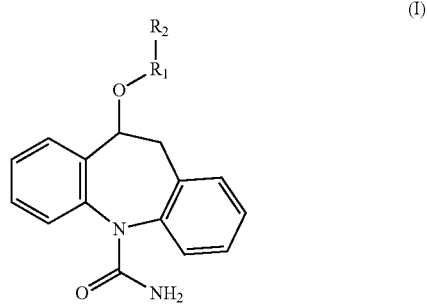

(I)

In certain embodiments, the present invention relates to the compounds and compositions of formula I, or pharmaceutically acceptable salts thereof,

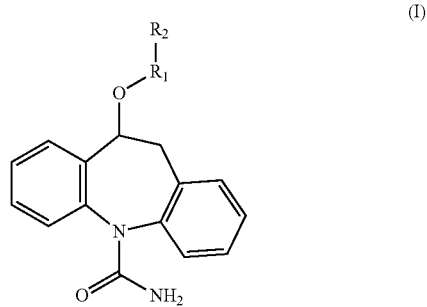

(I)

Wherein,
R¹ independently represents H, D, null,
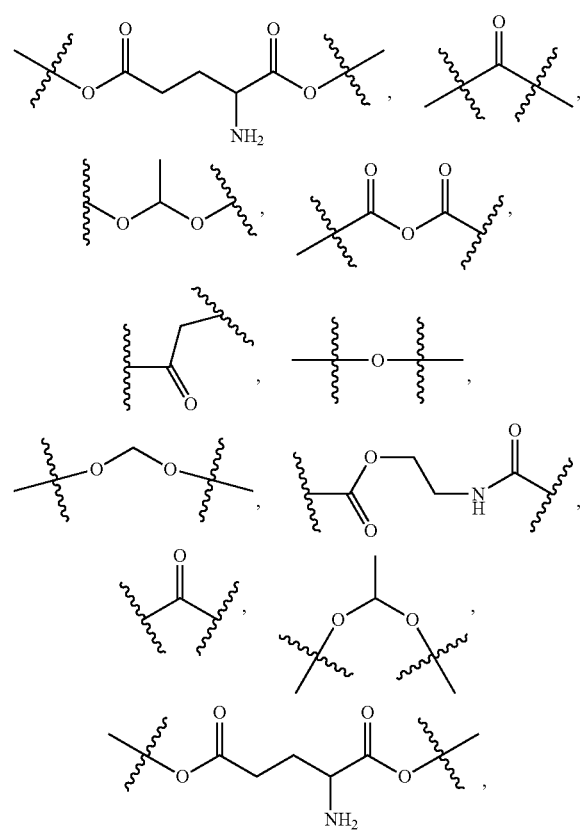
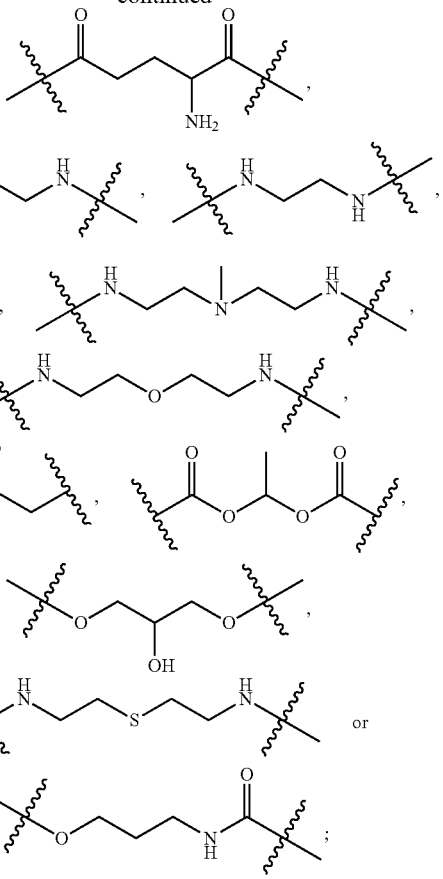
R² independently represents
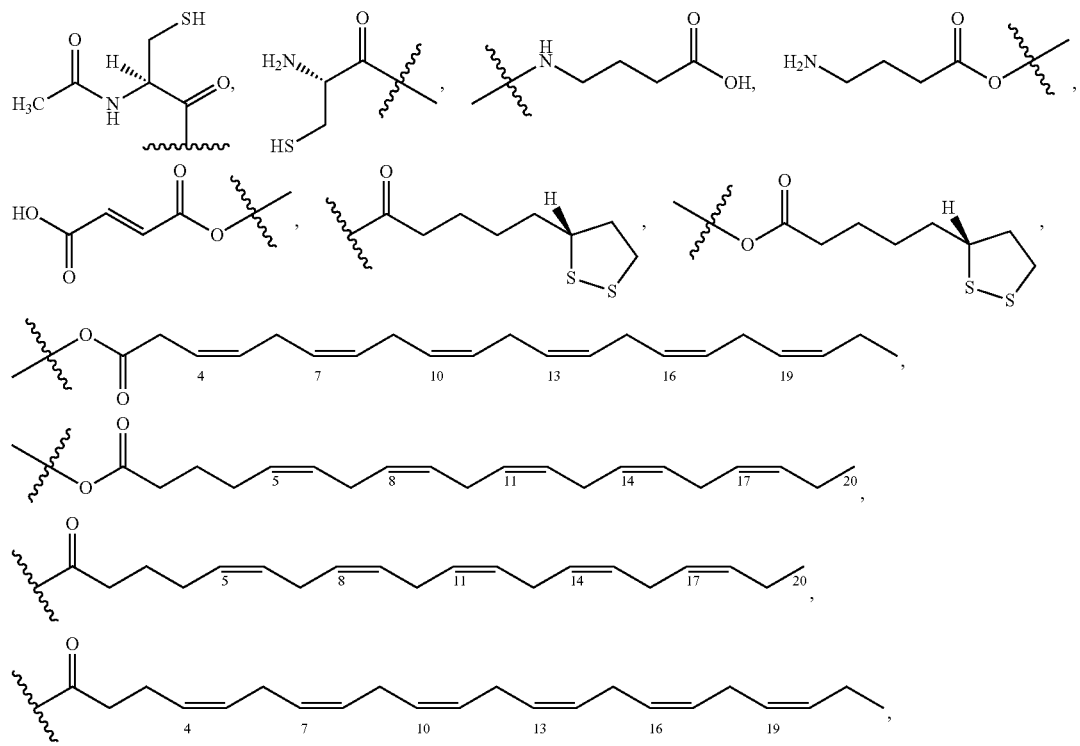

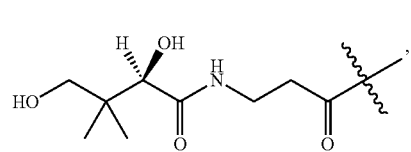 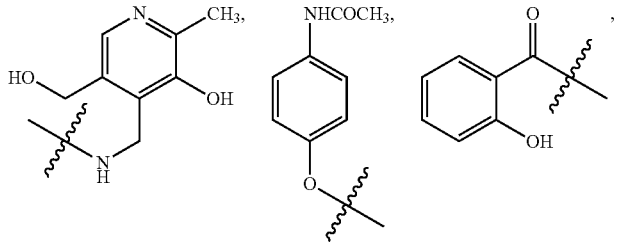

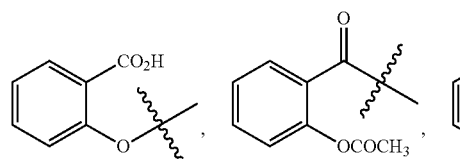 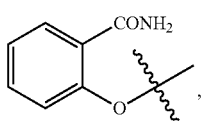 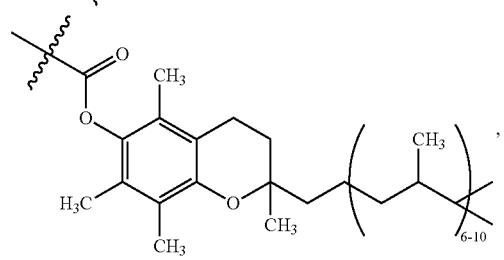

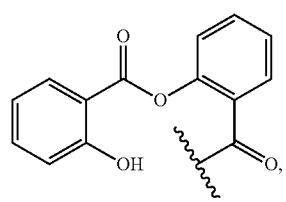 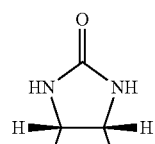 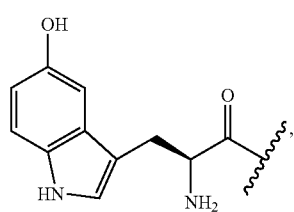

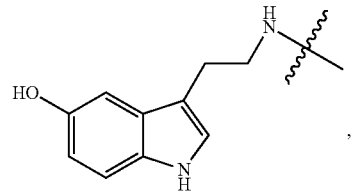 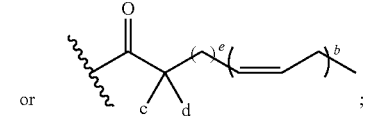

a is independently 2, 3 or 7;
each b is independently 3, 5 or 6;
e is independently 1, 2 or 6;
c and d are each independently H, D, —OH, —OD, $C_1$-$C_6$-alkyl, —$NH_2$ or —$COCH_3$.

In certain embodiments, the present invention relates to the compounds and compositions of formula (Ia) in a biologically active or S-enantiomer form or pharmaceutically acceptable salts thereof, Wherein,
$R^1$ each independently represents D, NULL,

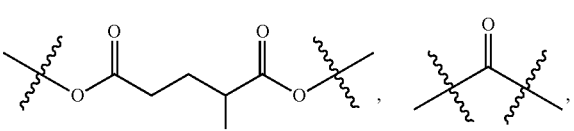

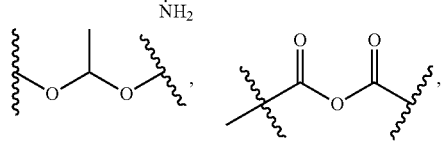

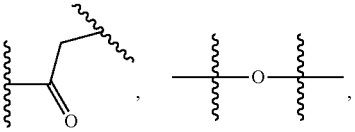

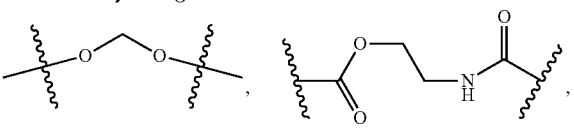

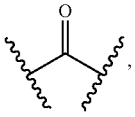 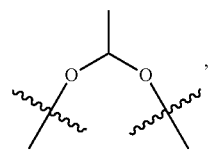

Formula Ia

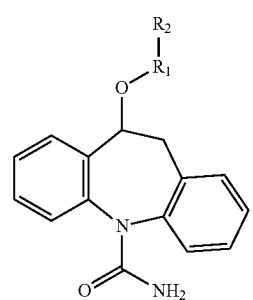

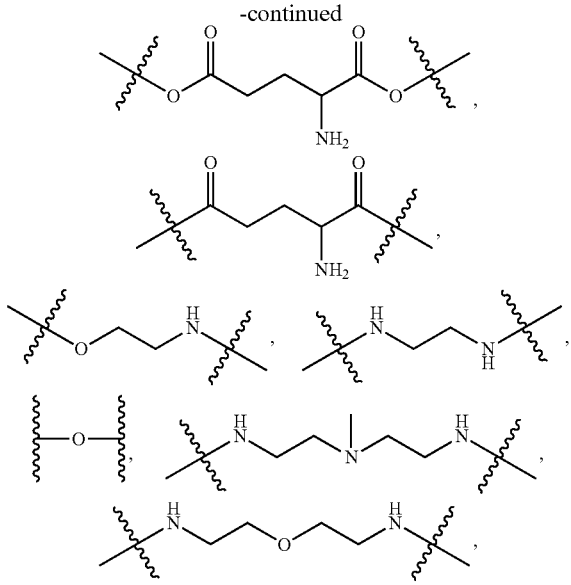
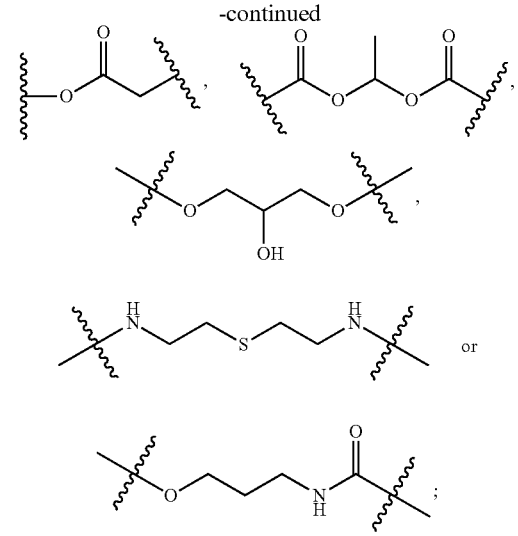
$R^2$ independently represents
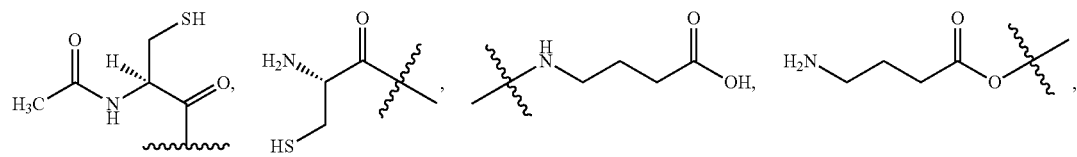
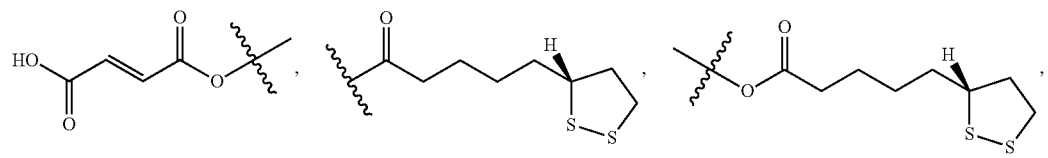
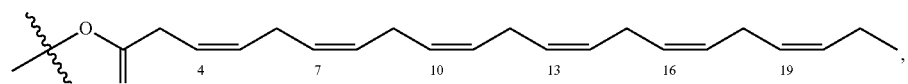
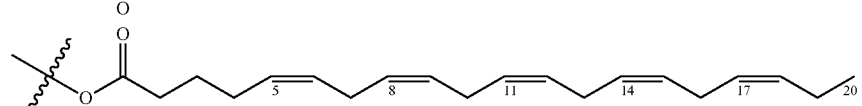
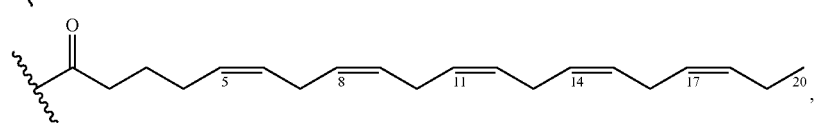
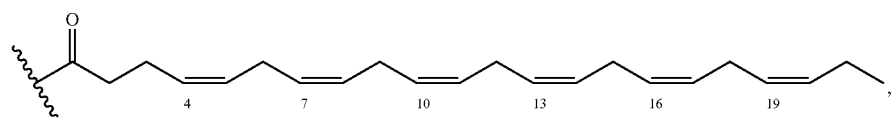
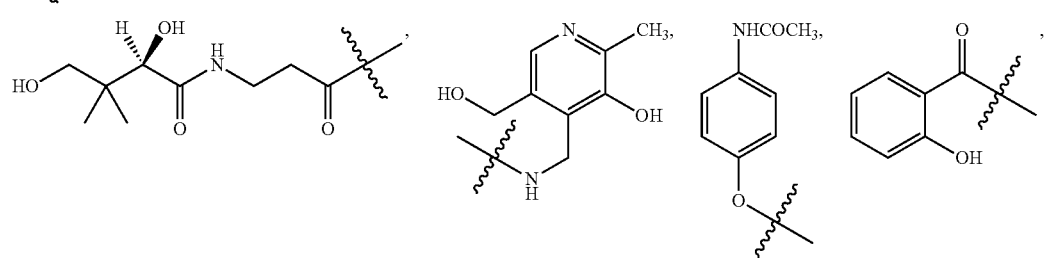

-continued

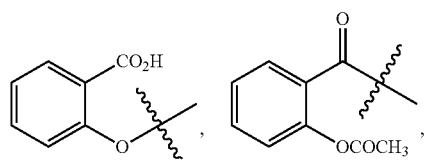 , 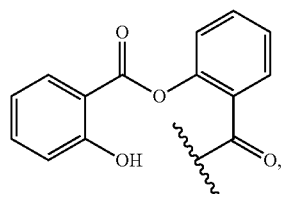 , 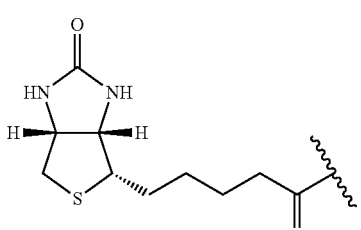 , 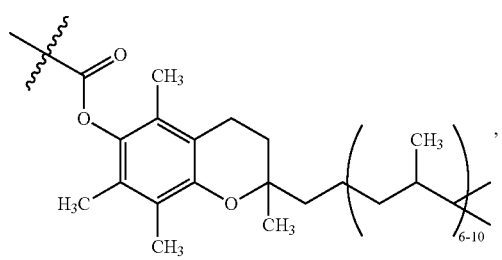

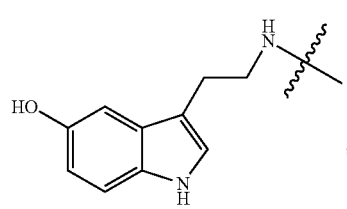 , 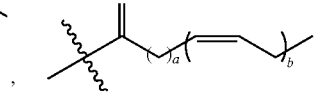 , 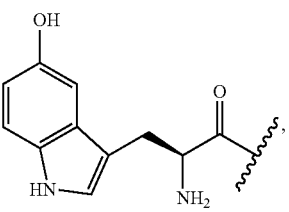

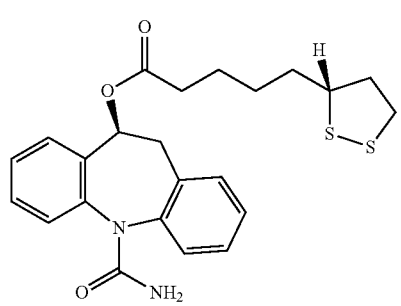 , 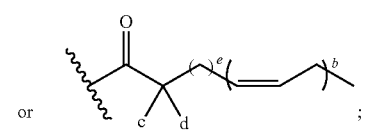 or 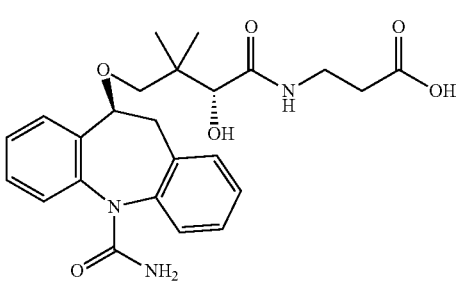 ;

a is independently 2, 3 or 7;
each b is independently 3, 5 or 6;
e is independently 1, 2 or 6;
c and d are each independently H, D, —OH, —OD, $C_1$-$C_6$-alkyl, —$NH_2$ or —$COCH_3$.

In the illustrative embodiments, examples of compounds of active stereoisomer form of formula I and formula Ia are as set forth below:

Herein the application also provides a kit comprising any of the pharmaceutical compositions disclosed herein. The kit may comprise instructions for use in the treatment of Epilepsy and neurological disorders or its related complications.

The application also discloses a pharmaceutical composition comprising a pharmaceutically acceptable carrier and any of the compositions herein. In some aspects, the pharmaceutical composition is formulated for systemic admin- (1-1)

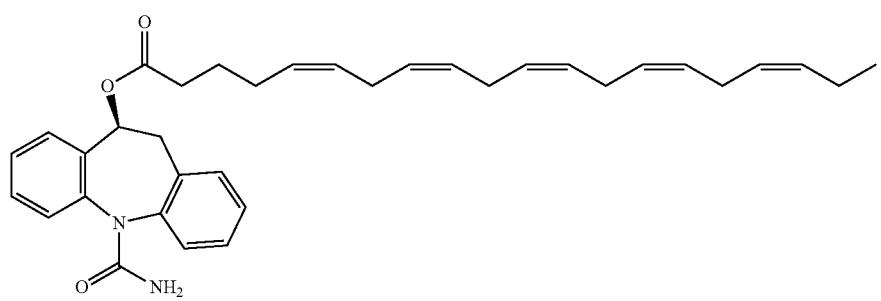

(1-2)

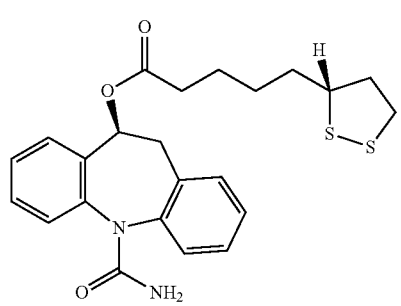

(1-3)

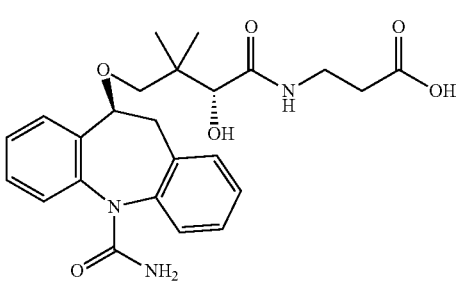

istration, oral administration, sustained release, parenteral administration, injection, subdermal administration, or transdermal administration.

Herein, the application additionally provides kits comprising the pharmaceutical compositions described herein. The kits may further comprise instructions for use in the treatment of Epilepsy and neurological disorders or its related complications.

The compositions described herein have several uses. The present application provides, for example, methods of treating a patient suffering from Epilepsy and neurological disorders or its related complications manifested from metabolic conditions, chronic diseases or disorders; Hepatology, Cancer, Neurological, Hematological, Orthopedic, Cardiovascular, Renal, Skin, Vascular or Ocular complications.

BRIEF DESCRIPTION OF FIGURES

Example embodiments are illustrated by way of example and not limitation in the figures of the accompanying drawings, in which like references indicate similar elements and in which.

DETAILED DESCRIPTION OF THE INVENTION

Definitions

Figure 1:
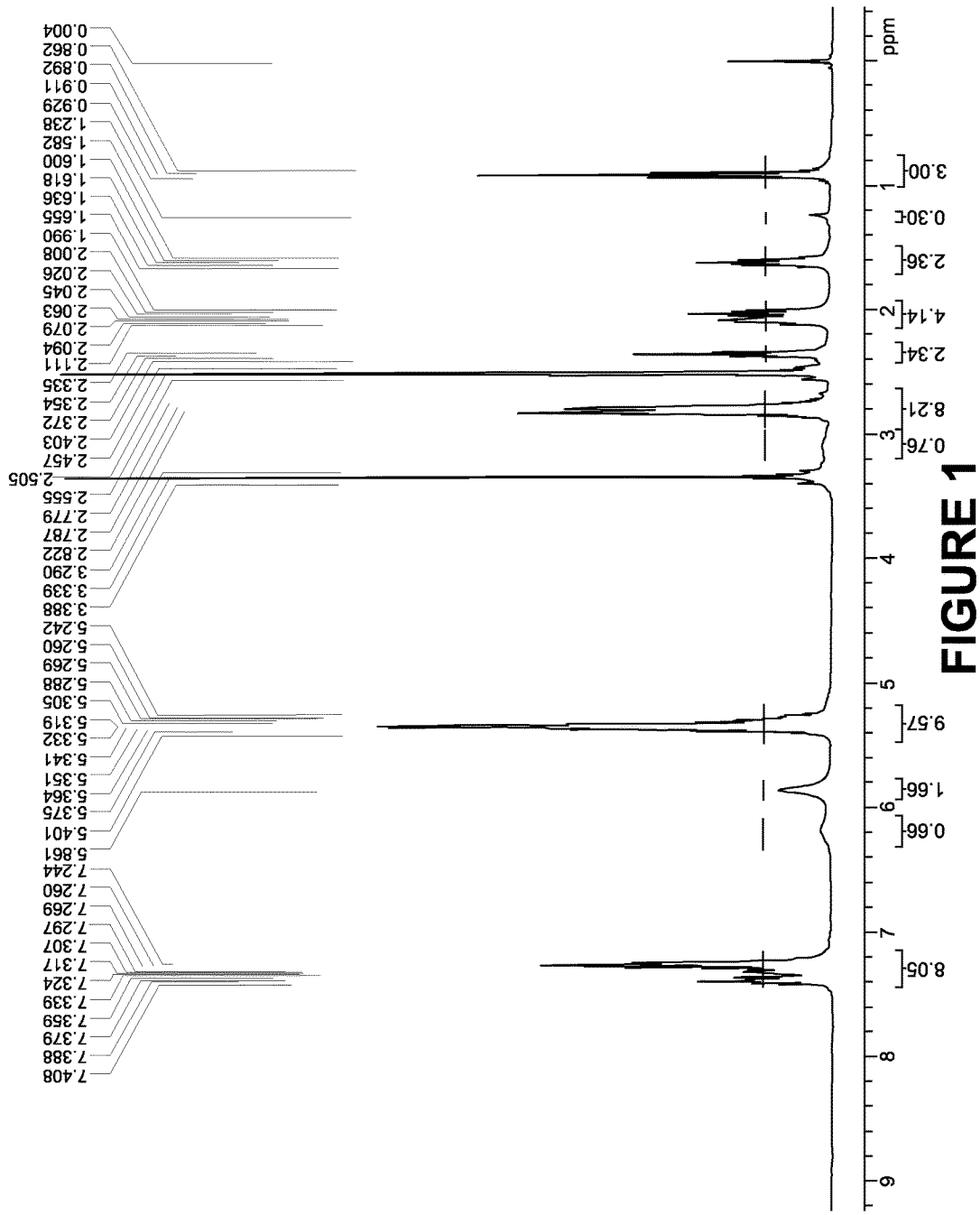
FIG. 1 shows the 1H-NMR results for Formula I.
Figure 2:
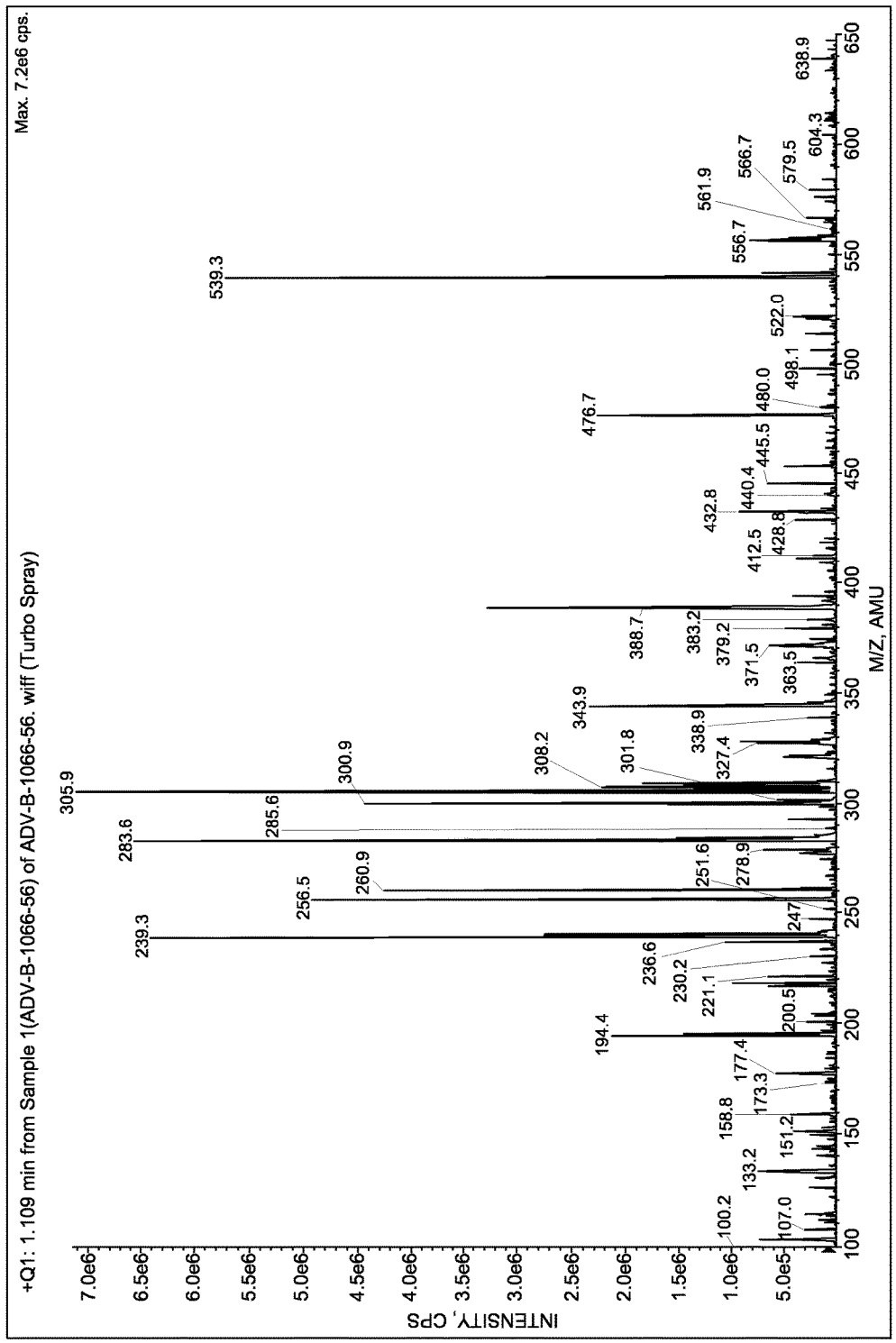
FIG. 2 shows the LC-MS results for Formula I.

As used herein, the following terms and phrases shall have the meanings set forth below. Unless defined otherwise, all technical and scientific terms used herein have the same meaning as commonly understood to one of ordinary skill in the art.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be affected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

As used herein, the term "metabolic condition" refers to an Inborn errors of metabolism (or genetic metabolic conditions) are genetic disorders that result from a defect in one or more metabolic pathways; specifically, the function of an enzyme is affected and is either deficient or completely absent. Metabolic condition associated diseases include: Hepatic, Neurologic, Psychiatric, Hematologic, Neurological, Renal, Cardiovascular, Cancer, Musculoskeletal, Orthopedic and Gastrointestinal.

The term "polymorph" as used herein is art-recognized and refers to one crystal structure of a given compound.

"Residue" is an art-recognized term that refers to a portion of a molecule. For instance, a residue of thioctic acid may be: dihydrolipoic acid, bisnorlipoic acid, tetranorlipoic acid, 6,8-bismethylmercapto-octanoic acid, 4,6-bismethylmercapto-hexanoic acid, 2,4-bismethylmeracapto-butanoic acid, 4,6-bismethylmercapto-hexanoic acid.

The phrases "parenteral administration" and "administered parenterally" as used herein refer to modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intra-articular, subcapsular, subarachnoid, intraspinal and intrastemal injection and infusion.

A "patient," "subject," or "host" to be treated by the subject method may mean either a human or non-human animal, such as primates, mammals, and vertebrates.

The phrase "pharmaceutically acceptable" is art-recognized. In certain embodiments, the term includes compositions, polymers and other materials and/or dosage forms which are, within the scope of sound medical judgment, suitable for use in contact with the tissues of mammals, human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, solvent or encapsulating material involved in carrying or transporting any subject composition, from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "polymorph" as used herein is art-recognized and refers to one crystal structure of a given compound.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic, (i.e., it is intended to diminish, ameliorate, or stabilize the existing unwanted condition or side effects thereof).

The term "predicting" as used herein refers to assessing the probability according to which a neurological condition or disorder such as epilepsy or neuropathic pain related diseases patient will suffer from abnormalities or complication and/or terminal platelet aggregation or failure and/or death (i.e. mortality) within a defined time window (predictive window) in the future. The mortality may be caused by the central nervous system or complication. The predictive window is an interval in which the subject will develop one or more of the said complications according to the predicted probability. The predictive window may be the entire remaining lifespan of the subject upon analysis by the method of the present invention. Preferably, however, the predictive window is an interval of one month, six months or one, two, three, four, five or ten years after appearance of the cardiovascular complication (more preferably and precisely, after the sample to be analyzed by the method of the present invention has been obtained). As will be understood by those skilled in the art, such an assessment is usually not intended to be correct for 100% of the subjects to be analyzed. The term, however, requires that the assessment will be valid for a statistically significant portion of the subjects to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction will be correct for at least 60%, at least 70%, at least 80%, or at least 90% of the subjects of a given cohort.

The term "treating" is art-recognized and includes preventing a disease, disorder or condition from occurring in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the vascular condition such as Epilepsy and neurological disorders condition of a subject by administration of an agent even though such agent does not treat the cause of the condition. The term "treating", "treat" or "treatment" as used herein includes curative, preventative (e.g., prophylactic), adjunct and palliative treatment.

Neurological diseases related disorders includes such as psychotic disorders, epilepsy, neuropathic pain, neuralgia and other related diseases or any other medical condition, is well understood in the art, and includes administration of a composition which reduces the frequency of, or delays the onset of, symptoms of a medical condition in a subject relative to a subject which does not receive the composition.

The phrase "therapeutically effective amount" is an art-recognized term. In certain embodiments, the term refers to an amount of a salt or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

In certain embodiments, the pharmaceutical compositions described herein are formulated in a manner such that said compositions will be delivered to a patient in a therapeutically effective amount, as part of a prophylactic or therapeutic treatment. The desired amount of the composition to be administered to a patient will depend on absorption, inactivation, and excretion rates of the drug as well as the delivery rate of the salts and compositions from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular salt or composition may be adjusted to accommodate variations in the treatment parameters. Such treatment parameters include the clinical use to which the preparation is put, e.g., the site treated, the type of patient, e.g., human or non-human, adult or child, and the nature of the disease or condition.

In certain embodiments, the dosage of the subject compositions provided herein may be determined by reference to the plasma concentrations of the therapeutic composition or other encapsulated materials. For example, the maximum plasma concentration (Cmax) and the area under the plasma concentration-time curve from time 0 to infinity may be used.

The term "solvate" as used herein, refers to a compound formed by solvation (e.g., a compound formed by the combination of solvent molecules with molecules or ions of the solute).

When used with respect to a pharmaceutical composition or other material, the term "sustained release" is art-recognized. For example, a subject composition which releases a substance over time may exhibit sustained release characteristics, in contrast to a bolus type administration in which the entire amount of the substance is made biologically available at one time. For example, in particular embodiments, upon contact with body fluids including blood, spinal fluid, mucus secretions, lymph or the like, one or more of the pharmaceutically acceptable excipients may undergo gradual or delayed degradation (e.g., through hydrolysis) with concomitant release of any material incorporated therein, e.g., an therapeutic and/or biologically active salt and/or composition, for a sustained or extended period (as compared to the release from a bolus). This release may result in prolonged delivery of therapeutically effective amounts of any of the therapeutic agents disclosed herein.

The phrases "systemic administration," "administered systemically," "peripheral administration" and "administered peripherally" are art-recognized, and include the administration of a subject composition, therapeutic or other material at a site remote from the disease being treated. Administration of an agent for the disease being treated, even if the agent is subsequently distributed systemically, may be termed "local" or "topical" or "regional" administration, other than directly into the central nervous system, e.g., by subcutaneous administration, such that it enters the patient's system and, thus, is subject to metabolism and other like processes.

The phrase "therapeutically effective amount" is an art-recognized term. In certain embodiments, the term refers to an amount of a salt or composition disclosed herein that produces some desired effect at a reasonable benefit/risk ratio applicable to any medical treatment. In certain embodiments, the term refers to that amount necessary or sufficient to eliminate or reduce medical symptoms for a period of time. The effective amount may vary depending on such factors as the disease or condition being treated, the particular targeted constructs being administered, the size of the subject, or the severity of the disease or condition. One of ordinary skill in the art may empirically determine the effective amount of a particular composition without necessitating undue experimentation.

The present disclosure also contemplates prodrugs of the compositions disclosed herein, as well as pharmaceutically acceptable salts of said prodrugs.

This application also discloses a pharmaceutical composition comprising a pharmaceutically acceptable carrier and the composition of a compound of Formula I may be formulated for systemic or topical or oral administration. The pharmaceutical composition may be also formulated for oral administration, oral solution, injection, subdermal administration, or transdermal administration. The pharmaceutical composition may further comprise at least one of a pharmaceutically acceptable stabilizer, diluent, surfactant, filler, binder, and lubricant.

In many embodiments, the pharmaceutical compositions described herein will incorporate the disclosed compounds and compositions (Formulas I) to be delivered in an amount sufficient to deliver to a patient a therapeutically effective amount of a compound of formula I or composition as part of a prophylactic or therapeutic treatment. The desired concentration of formula I or its pharmaceutical acceptable salts will depend on absorption, inactivation, and excretion rates of the drug as well as the delivery rate of the salts and compositions from the subject compositions. It is to be noted that dosage values may also vary with the severity of the condition to be alleviated. It is to be further understood that for any particular subject, specific dosage regimens should be adjusted over time according to the individual need and the professional judgment of the person administering or supervising the administration of the compositions. Typically, dosing will be determined using techniques known to one skilled in the art.

Additionally, the optimal concentration and/or quantities or amounts of any particular compound of formula I may be adjusted to accommodate variations in the treatment parameters. Such treatment parameters include the clinical use to which the preparation is put, e.g., the site treated, the type of patient, e.g., human or non-human, adult or child, and the nature of the disease or condition.

The concentration and/or amount of any compound of formula I may be readily identified by routine screening in animals, e.g., rats, by screening a range of concentration and/or amounts of the material in question using appropriate assays. Known methods are also available to assay local tissue concentrations, diffusion rates of the salts or compositions, and local blood flow before and after administration of therapeutic formulations disclosed herein. One such method is microdialysis, as reviewed by T. E. Robinson et al., 1991, microdialysis in the neurosciences, Techniques, volume 7, Chapter 1. The methods reviewed by Robinson may be applied, in brief, as follows. A microdialysis loop is placed in situ in a test animal. Dialysis fluid is pumped through the loop. When compounds with formula I such as those disclosed herein are injected adjacent to the loop, released drugs are collected in the dialysate in proportion to their local tissue concentrations. The progress of diffusion of the salts or compositions may be determined thereby with suitable calibration procedures using known concentrations of salts or compositions.

In certain embodiments, the dosage of the subject compounds of formula I provided herein may be determined by reference to the plasma concentrations of the therapeutic composition or other encapsulated materials. For example, the maximum plasma concentration (Cmax) and the area under the plasma concentration-time curve from time 0 to infinity may be used.

Generally, in carrying out the methods detailed in this application, an effective dosage for the compounds of Formulas I is in the range of about 0.01 mg/kg/day to about 100 mg/kg/day in single or divided doses, for instance 0.01 mg/kg/day to about 50 mg/kg/day in single or divided doses. The compounds of Formulas I may be administered at a dose of, for example, less than 0.2 mg/kg/day, 0.5 mg/kg/day, 1.0 mg/kg/day, 5 mg/kg/day, 10 mg/kg/day, 20 mg/kg/day, 30 mg/kg/day, or 40 mg/kg/day. Compounds of Formula I may also be administered to a human patient at a dose of, for example, between 0.1 mg and 1000 mg, between 5 mg and 80 mg, or less than 1.0, 9.0, 12.0, 20.0, 50.0, 75.0, 100, 300, 400, 500, 800, 1000 mg per day. In certain embodiments, the compositions herein are administered at an amount that is less than 95%, 90%, 80%, 70%, 60%, 50%, 40%, 30%, 20%, or 10% of the compound of formula I required for the same therapeutic benefit.

An effective amount of the compounds of formula I described herein refers to the amount of one of said salts or compositions which is capable of inhibiting or preventing a disease. For example epilepsy and neurological disorders, epilepsy, neuropathic pain, psychosis or any other neurological medical condition.

An effective amount may be sufficient to prohibit, treat, alleviate, ameliorate, halt, restrain, slow or reverse the progression, or reduce the severity of a complication resulting from nerve damage or demyelization and/or elevated reactive oxidative-nitrosative species and/or abnormalities in neurotransmitter homeostasis's, in patients who are at risk for such complications. As such, these methods include both medical therapeutic (acute) and/or prophylactic (prevention) administration as appropriate. The amount and timing of compositions administered will, of course, be dependent on the subject being treated, on the severity of the affliction, on the manner of administration and on the judgment of the prescribing physician. Thus, because of patient-to-patient variability, the dosages given above are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases.

The compositions provided by this application may be administered to a subject in need of treatment by a variety of conventional routes of administration, including orally, topically, parenterally, e.g., intravenously, subcutaneously or intramedullary. Further, the compositions may be administered intranasally, as a rectal suppository, or using a "flash" formulation, i.e., allowing the medication to dissolve in the mouth without the need to use water. Furthermore, the compositions may be administered to a subject in need of treatment by controlled release dosage forms, site specific drug delivery, transdermal drug delivery, patch (active/passive) mediated drug delivery, by stereotactic injection, or in nanoparticles.

The compositions may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compositions and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as L-arginine, sodium citrate, calcium carbonate and calcium phosphate may be employed along with various disintegrates such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Appropriate materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof. The compounds of formula I may also comprise enterically coated comprising of various excipients, as is well known in the pharmaceutical art.

For parenteral administration, solutions of the compositions may be prepared in (for example) sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

The formulations, for instance tablets, may contain e.g. 10 to 100, 50 to 250, 150 to 500 mg, or 350 to 800 mg e.g. 10, 50, 100, 300, 500, 700, 800 mg of the compounds of formula I disclosed herein, for instance, compounds of formula I or pharmaceutical acceptable salts of a compounds of Formula I.

Generally, a composition as described herein may be administered orally, or parenterally (e.g., intravenous, intramuscular, subcutaneous or intramedullary). Topical administration may also be indicated, for example, where the patient is suffering from gastrointestinal disorder that prevent oral administration, or whenever the medication is best applied to the surface of a tissue or organ as determined by the attending physician. Localized administration may also be indicated, for example, when a high dose is desired at the target tissue or organ. For buccal administration the active composition may take the form of tablets or lozenges formulated in a conventional manner.

The dosage administered will be dependent upon the identity of the neurological disease; the type of host involved, including its age, health and weight; the kind of concurrent treatment, if any; the frequency of treatment and therapeutic ratio.

Illustratively, dosage levels of the administered active ingredients are: intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight.

Expressed in terms of concentration, an active ingredient can be present in the compositions of the present invention for localized use about the cutis, intranasally, pharyngolaryngeally, bronchially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions of suspensions, and oral solutions or suspensions and the like, containing suitable quantities of an active ingredient. For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like.

The powder mixture can be granulated by wetting with a binder such as corn syrup, gelatin solution, methylcellulose solution or acacia mucilage and forcing through a screen. As an alternative to granulating, the powder mixture can be slugged, i.e., ran through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active, ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid unit dosage form is prepared utilizing an active ingredient and a suitable pharmaceutical vehicle, preferably P.F. water, a dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The tablets of the present invention contain one or more pharmaceutically active agents that are released therefrom upon contact of the tablet with a liquid medium, for example a dissolution medium such as gastrointestinal fluids. "Water soluble," as used herein in connection with non-polymeric materials, shall mean from sparingly soluble to very soluble, i.e., not more than 100 parts water required to dissolve 1 part of the non-polymeric, water soluble solute. See Remington, The Science and Practice of Pharmacy, pp 208-209 (2000). "Water soluble," as used herein in connection with polymeric materials, shall mean that the polymer swells in water and can be dispersed at the molecular level or dissolved in water.

As used herein, the term "modified release" shall apply to tablets, matrices, particles, coatings, portions thereof, or compositions that alter the release of an pharmaceutically active agent in any manner. Types of modified release include controlled, prolonged, sustained, extended, delayed, pulsatile, repeat action, and the like. Suitable mechanisms for achieving these types of modified release include diffusion, erosion, surface area control via geometry and/or impermeable barriers, or other mechanisms known in the art.

In one embodiment of the invention, the first pharmaceutically active agent and the hydrophilic polymer are mixed with a powder containing a pharmaceutically-acceptable carrier, which is also defined herein as the tablet matrix. In one embodiment, the powder has an average particle size of about 50 microns to about 500 microns, such as between 50 microns and 300 microns. Particles in this size range are particularly useful for direct compression processes. In embodiment, the components of powder are blended together, for example as dry powders, and fed into the die cavity of an apparatus that applies pressure to form a tablet core. Any suitable compacting apparatus may be used, including, but not limited to, conventional unitary or rotary tablet press. In one embodiment, the tablet core may be formed by compaction using a rotary tablet press (e.g., such as those commercially available from Fette America Inc., Rockaway, N.J., or Manesty Machines LTD, Liverpool, UK). In general, a metered volume of powder is filled into a die cavity (where the powder is either gravity fed or mechanically fed from a feeder) of the rotary tablet press, and the cavity rotates as part of a "die table" from the filling position to a compaction position. At the compaction position, the powder is compacted between an upper and a lower punch, then the resulting tablet core is pushed from the die cavity by the lower punch and then guided to an injection chute by a stationary "take-off bar.

In one embodiment of the invention, the tablet core may be a directly compressed tablet core made from a powder that is substantially free of water-soluble polymeric binders and hydrated polymers. As used herein, what is meant by "substantially free" is less than 5 percent, such as less than 1 percent, such as less than 0.1 percent, such as completely free (e.g., 0 percent). This composition is advantageous for minimizing processing and material costs and providing for optimal physical and chemical stability of the tablet core. In one embodiment, the density of the tablet core is greater than about 0.9 g/cc.

The tablet core may have one of a variety of different shapes. For example, the tablet core may be shaped as a polyhedron, such as a cube, pyramid, prism, or the like; or may have the geometry of a space figure with some non-flat faces, such as a cone, truncated cone, cylinder, sphere, torus, or the like. In certain embodiments, a tablet core has one or more major faces. For example, the tablet core surface typically has opposing upper and lower faces formed by contact with the upper and lower punch faces in the compression machine. In such embodiments the tablet core surface typically further includes a "belly-band" located between the upper and lower faces, and formed by contact with the die walls in the compression machine.

As discussed above, the tablet core contains one or more hydrophilic polymers. Suitable hydrophilic polymers include, but are not limited to, water swellable cellulose derivatives, polyalkylene glycols, thermoplastic polyalkylene oxides, acrylic polymers, hydrocolloids, clays, gelling starches, swelling cross-linked polymers, and mixtures thereof. Examples of suitable water swellable cellulose derivatives include, but are not limited to, sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols include, but are not limited to, polyethylene glycol. Examples of suitable thermoplastic polyalkylene oxides include, but are not limited to, poly(ethylene oxide). Examples of suitable acrylic polymers include, but are not limited to, potassium methacrylatedivinylbenzene copolymer, polymethylmethacrylate, high-molecular weight crosslinked acrylic acid homopolymers and copolymers such as those commercially available from Noveon Chemicals under the tradename CARBOPOL™. Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and mixtures thereof. Examples of suitable gelling starches include, but are not limited to, acid hydrolyzed starches, swelling starches such as sodium starch glycolate and derivatives thereof, and mixtures thereof. Examples of suitable swelling cross-linked polymers include, but are not limited to, cross-linked polyvinyl pyrrolidone, cross-linked agar, and cross-linked carboxymethylcellulose sodium, and mixtures thereof.

In one embodiment, an osmogen is incorporated into the tablet core in order to draw water into the tablet upon contact with fluids, such as gastrointestinal fluids. An osmogen as used herein is a water soluble component which preferentially draws water into the tablet core for the purposes of distributing the water throughout the core, so that the active ingredient contained in the core may be released. In one embodiment the osmogen is a salt such as but not limited to sodium chloride, potassium chloride, sodium citrate, or potassium citrate.

The carrier may contain one or more suitable excipients for the formulation of tablets. Examples of suitable excipients include, but are not limited to, fillers, adsorbents, binders, disintegrants, lubricants, glidants, release-modifying excipients, superdisintegrants, antioxidants, and mixtures thereof.

Suitable fillers include, but are not limited to, water-soluble compressible carbohydrates such as sugars (e.g., dextrose, sucrose, maltose, and lactose), starches (e.g., corn starch), sugar-alcohols (e.g., mannitol, sorbitol, maltitol, erythritol, and xylitol), starch hydrolysates (e.g., dextrins, and maltodextrins), and water insoluble plastically deforming materials (e.g., microcrystalline cellulose or other cellulosic derivatives), and mixtures thereof. Suitable adsorbents (e.g., to adsorb the liquid drug composition) include, but are not limited to, water-insoluble adsorbents such as dicalcium phosphate, tricalcium phosphate, silicified microcrystalline cellulose (e.g., such as distributed under the PROSOLV brand (PenWest Pharmaceuticals, Patterson, N.Y.)), magnesium aluminometasilicate (e.g., such as distributed under the NEUSILIN™ brand (Fuji Chemical Industries (USA) Inc., Robbinsville, N.J.), clays, silicas, bentonite, zeolites, magnesium silicates, hydrotalcite, veegum, and mixtures thereof.

Suitable binders include, but are not limited to, dry binders such as polyvinyl pyrrolidone and hydroxypropylmethylcellulose; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pus stulan, laminarin, scleroglucan, inulin, whelan, rhamsan, zooglan, methylan, chitin, cyclodextrin, chitosan, polyvinyl pyrrolidone, cellulosics, sucrose, and starches; and mixtures thereof. Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their salts, such as magnesium stearate and stearic acid, talc, glycerides waxes, and mixtures thereof. Suitable glidants include, but are not limited to, colloidal silicon dioxide. Suitable release-modifying excipients include, but are not limited to, insoluble edible materials, pH-dependent polymers, and mixtures thereof.

Suitable insoluble edible materials for use as release-modifying excipients include, but are not limited to, water-insoluble polymers and low-melting hydrophobic materials, copolymers thereof, and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers, copolymers thereof, and mixtures thereof. Suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their salts, and mixtures thereof. Examples of suitable fatty acid esters include, but are not limited to, sucrose fatty acid esters, mono-, di-, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate, and mixtures thereof. Examples of super disintegrants include, but are not limited to, croscarmellose sodium, sodium starch glycolate and cross-linked povidone (crospovidone). In one embodiment the tablet core contains up to about 5 percent by weight of such super disintegrant.

Examples of antioxidants include, but are not limited to, tocopherols, ascorbic acid, sodium pyrosulfite, butylhydroxytoluene, butylated hydroxyanisole, edetic acid, and edetate salts, and mixtures thereof. Examples of preservatives include, but are not limited to, citric acid, tartaric acid, lactic acid, malic acid, acetic acid, benzoic acid, and sorbic acid, and mixtures thereof.

The osmotic tablets of the present invention include an osmotic coating. An osmotic coating is one that is semipermeable thereby allows water to be drawn into the tablet core, e.g., for the purposes of releasing the active ingredient such as through a pre-made hole in the coating or through coating itself it is semipermeable membrane. The osmotic coating, thus, does not fully dissolve upon contact with water In one embodiment, the osmotic coating contains a water soluble component such as a water solible film former which aids in facilitating a further influx of water upon contact with water. In the current invention the osmotic coating is applied via spray coating. Suitable spray coating techniques include spray coating via a coating pan or fluid bed process such as Wurster coating or top spray fluid bed coating as described in the text, "The Theory and Practice of Industrial Pharmacy", Lachman, Leon et. al, 3rd ed. The osmotic coating may be applied using a solution prepared with water, organic solvents, or mixtures thereof. Suitable organic solvents include but are not limited to acetone, isopropanol, methylene chloride, hexane, methanol, ethanol, and mixtures thereof. In one embodiment the polymer(s) are dissolved in the coating solution. In one embodiment, the polymer(s) are dispersed, as is the case when applying water insoluble polymers via a dispersion or as is the case when using ethylcellulose dispersions.

In one embodiment in which the osmotic coating functions as a semipermeable membrane (e.g., allowing water or solvent to pass into the core, but being impermeable to dissolved pharmaceutically active agent, thereby preventing the passage of pharmaceutically active agent therethrough) the film former is selected from water insoluble polymers, pH-dependent polymers, water soluble polymers, and combinations thereof. In one embodiment, the osmotic coating includes a water insoluble polymer and a pore forming material. Examples of suitable water-insoluble polymers include ethylcellulose, polyvinyl alcohols, polyvinyl acetate, polycaprolactones, cellulose acetate and its derivatives, acrylates, methacrylates, acrylic acid copolymers, and combinations thereof. In one embodiment, the water insoluble polymer is cellulose acetate. In one embodiment, the osmotic coating includes from about 10 to about 100 weight percent of a water insoluble film former.

In one embodiment of the osmotic coating, the water insoluble polymer is combined with a water soluble film former in order to create pores in the resulting semipermeable membrane. Examples of suitable film formers include, but are not limited to: water soluble vinyl polymers such as polyvinylalcohol (PVA); water soluble polycarbohydrates such as hydroxypropyl starch, hydroxyethyl starch, pullulan, methylethyl starch, carboxymethyl starch, pregelatinized starches, and film-forming modified starches; water swellable cellulose derivatives such as hydroxypropyl cellulose (HPC), hydroxypropylmethyl cellulose (HPMC), methyl cellulose (MC), hydroxyethylmethylcellulose (HEMC), hydroxybutylmethylcellulose (HBMC), hydroxyethylethylcellulose (HEEC), and hydroxyethylhydroxypropylmethyl cellulose (HEMPMC); water soluble copolymers such as methacrylic acid and methacrylate ester copolymers, polyvinyl alcohol and polyethylene glycol copolymers, polyethylene oxide and polyvinylpyrrolidone copolymers; and mixtures thereof.

In one embodiment, a pH dependent polymer is incorporated into the osmotic coating. In one embodiment, the pH dependent polymer is used at a level of from about 10 to about 50 percent by weight of the osmotic coating. Suitable film-forming pH-dependent polymers include, but are not limited to, enteric cellulose derivatives, such as for example hydroxypropyl methylcellulose phthalate, hydroxypropyl methylcellulose acetate succinate, and cellulose acetate phthalate; natural resins such as shellac and zein; enteric acetate derivatives such as polyvinylacetate phthalate, cellulose acetate phthalate, and acetaldehyde dimethylcellulose acetate; and enteric acrylate derivatives such as for example polymethacrylate-based polymers such as poly(methacrylic acid, methyl methacrylate) 1:2 (commercially available from Rohm Pharma GmbH under the tradename EUDRAGIT STM), and poly(methacrylic acid, methyl methacrylate) 1:1 (commercially available from Rohm Pharma GmbH under the tradename EUDRAGIT LTM); and combinations thereof. In one embodiment, the osmotic coating has an average thickness of at least 5 microns, such as from about 10 microns to about 200 microns, e.g. from about 20 microns to about 150 microns, e.g. from about 30 to about 150 microns. In one embodiment, the osmotic coating is free of porosity (e.g., wherein the pore volume is in a pore diameter range of less than 0.01 g/cc). In one embodiment, the average pore diameter of the osmotic coating is less than about 0.2 microns (e.g., less than about 0.15 microns).

In one embodiment, the osmotic coating is substantially free of anpharmaceutically active agent. In one embodiment the osmotic coating includes anpharmaceutically active agent which is different than the pharmaceutically active agent included in the immediate release coating. In one embodiment, the osmotic coating includes a plasticizer. In one embodiment the plasticizer must be of sufficient quantity to withstand the compression force of the immediate release coating. Suitable plasticizers include, but are not limited to: polyethylene glycol; propylene glycol; glycerin; sorbitol; triethyl citrate; tributyl citrate; dibutyl sebecate; vegetable oils such as castor oil, grape oil, olive oil, and sesame oil; surfactants such as polysorbates, sodium lauryl sulfates, and dioctyl-sodium sulfosuccinates; mono acetate of glycerol; diacetate of glycerol; triacetate of glycerol; natural gums; triacetin; acetyltributyl citrate; diethyloxalate; diethylmalate; diethyl fumarate; diethylmalonate; dioctylphthalate; dibutylsuccinate; glycerol tributyrate; hydrogenated castor oil; fatty acids such as lauric acid; glycerides such as mono-, di-, and/or triglycerides, which may be substituted with the same or different fatty acids groups such as, for example, stearic, palmitic, and oleic and the like; and mixtures thereof. In one embodiment, the plasticizer is triethyl citrate.

In one embodiment, at least about 50 percent of the cross-sectional area of the osmotic coating used in tablets of this invention is striated, such as at least about 80% of the cross-sectional area of the osmotic coating portion is striated. As used herein, "striated" means non-homogeneous with respect to appearance and with respect to the internal structure of the coating portion when viewed under any magnification and lighting conditions, at which point striations or layers can be viewed. Compressed portions of a pharmaceutical oral dosage forms do not display striated areas, wherein spray coated portions display striations. For example a crosssection of the osmotic coating portion is striated, and nonuniform with respect to refractive properties when observed utilizing a light microscope or a scanning electron microscope at a magnification of about 50 to about 400 times. The characteristic striations are indicative of the spray-coating process consisting of multiple repetitions of the steps consisting of: (a) application via spraying of coating solution; followed by (b) warm air drying, to a tumbling bed of tablets in a revolving coating pan such that numerous layers of coating material are built up as each application of coating material dries to form a layer. In one embodiment, the thickness of an individual striated layer is the range of about 10 microns to about 15 microns.

In certain embodiments, the osmotic coating is semipermeable (e.g., containing a plurality of small opening) and does not require the addition of an additional opening via laser or other means. In one such embodiment, the semipermeable membrane of the osmotic coating also allows for the release of the active ingredient in the tablet core through the membrane in a zero-order or first-order release manner.

In one embodiment, the immediate release coating has an average thickness of at least 50 microns, such as from about 50 microns to about 2500 microns; e.g., from about 250 microns to about 1000 microns. In embodiment, the immediate release coating is typically compressed at a density of more than about 0.9 g/cc, as measured by the weight and volume of that specific layer.

In one embodiment, the immediate release coating contains a first portion and a second portion, wherein at least one of the portions contains the second pharmaceutically active agent. In one embodiment, the portions contact each other at a center axis of the tablet. In one embodiment, the first portion includes the first pharmaceutically active agent and the second portion includes the second pharmaceutically active agent.

In one embodiment, the first portion contains the first pharmaceutically active agent and the second portion contains the second pharmaceutically active agent. In one embodiment, one of the portions contains a third pharmaceutically active agent. In one embodiment one of the portions contains a second immediate release portion of the same pharmaceutically active agent as that contained in the tablet core.

In one embodiment, the outer coating portion is prepared as a dry blend of materials prior to addition to the coated tablet core. In another embodiment the outer coating portion is included of a dried granulation including the pharmaceutically active agent.

In one embodiment, a suitable flavor or aroma agent may be added to the outer coating. Examples of suitable flavor and aroma agents include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavor of the fruit (e.g., strawberry, raspberry, and black currant); artificial and natural flavors of brews and liquors (e.g., cognac, whisky, rum, gin, sherry, port, and wine); tobacco, coffee, tea, cocoa, and mint; fruit juices including expelled juice from washed, scrubbed fruits such as lemon, orange, and lime; mint; ginger; cinnamon; cacoe/cocoa; vanilla; liquorice; menthol; eucalyptus; aniseeds nuts (e.g., peanuts, coconuts, hazelnuts, chestnuts, walnuts, and colanuts); almonds; raisins; and powder, flour, or vegetable material parts including tobacco plant parts (e.g., the genus *Nicotiana* in amounts not contributing significantly to a level of therapeutic nicotine), and mixtures thereof.

Formulations with different drug release mechanisms described above could be combined in a final dosage form containing single or multiple units. Examples of multiple units include multilayer tablets, capsules containing tablets, beads, or granules in a solid or liquid form. Typical, immediate release formulations include compressed tablets, gels, films, coatings, liquids and particles that can be encapsulated, for example, in a gelatin capsule. Many methods for preparing coatings, covering or incorporating drugs, are known in the art.

The immediate release dosage, unit of the dosage form, i.e., a tablet, a plurality of drug-containing beads, granules or particles, or an outer layer of a coated core dosage form, contains a therapeutically effective quantity of the active agent with conventional pharmaceutical excipients. The immediate release dosage unit may or may not be coated, and may or may not be admixed with the delayed release dosage unit or units (as in an encapsulated mixture of immediate release drug-containing granules, particles or beads and delayed release drug-containing granules or beads). A preferred method for preparing immediate release tablets (e.g., as incorporated into a capsule) is by compressing a drugcontaining blend, e.g., blend of granules, prepared using a direct, blend, wet-granulation or dry-granulation process. Immediate release tablets may also be molded rather than compressed, starting with a moist material containing a suitable water-soluble lubricant. However, preferred tablets described herein are manufactured using compression rather than molding. A preferred method for forming immediate release drug-containing blend is to mix drug particles directly with one or more excipients such as diluents (or fillers), binders, disintegrants, lubricants, glidants, and/or colorants. As an alternative to direct blending, a drug-containing blend may be prepared by using a wet-granulation or dry-granulation process. Beads containing the active agent may also be prepared by any one of a number of conventional techniques, typically starting from a fluid dispersion. For example, a typical method for preparing drug-containing beads involves blending the active agent with conventional pharmaceutical excipients such as microcrystalline cellulose, starch, polyvinylpyrrolidone, methylcellulose, talc, metallic stearates, and silicone dioxide. The admixture is used to coat a bead core such as a sugar sphere (e.g., "non-parcil") having a size of approximately 20 to 60 mesh.

An alternative procedure forpreparing drug beads is by blending tile drug with one or more pharmaceutically acceptable excipients, such as microcrystalline cellulose, lactose, cellulose, polyvinyl pyrrolidone, talc, magnesium stearate, and a disintegrant, extruding the blend, spheronizing the extrudate, drying and optionally coating the bead to form immediate release beads.

Extended release formulations are generally prepared as diffusion or osmotic systems, for example, as described in "Remington—The Science and Practice of Pharmacy", 20th. Ed., Lippincott Williams & Wilkins, Baltimore, Md., 2000). A diffusion system typically consists of one of two types of devices, reservoir and matrix, which are wellknown and described in die art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but are not limited to, methyl acrylate-methyl methacrylate, polyvinyl chloride, and polyethylene. Hydrophilic polymers include, but are not limited to, methylcellulose, hydroxypropylcellulose, hydorxypropylmethylcellulose, sodium carboxymethylcellulose, and Carbopol™ 934, and polyethylene oxides. Fatty compounds include, but are not limited to, various waxes such as carnauba wax and glyceryl tristearate. Alternatively, extended release formulations can be prepared using osmotic systems or by applying a semi-permeable coating to the dosage form. In the latter case, the desired drug release profile can be achieved by combining, low permeability and high permeability coating materials in suitable proportion.

An immediate release portion can be added to the extended release system by means of either applying an immediate release layer on top of the extended release core; using coating or compression processes or in a multiple unit system such as a capsule containing extended and immediate release beads.

Extended release tablets containing hydrophilic polymers are prepared by techniques commonly known in the art such as direct compression, wet granulation, or dry granulation processes. These formulations usually incorporate polymers, diluents, binders, and lubricants as well as the active pharmaceutical ingredient. The usual diluents include inert powdered substances such as different kinds of starch, powdered, cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethycellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils. Extended release tablets containing wax materials are generally prepared using methods known in the art such as a direct blend method, a congealing method, and an aqueous dispersion method. In the congealing method, the drug is mixed with a wax material and either spray-congealed or congealed and screened and processed.

Delayed release dosage formulations are created by coating a solid dosage form with a film of a polymer which is insoluble in the acid environment of the stomach, but soluble in the neutral environment of small intestines. The delayed release dosage units can be prepared, for example, by coating a drug or a drug-containing composition with a selected coating material. The drug-containing composition may be a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydoxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT™ (Rohm Pharma; [0086] Westerstadt, Germany), including EUDRAGIT™ L30D-55 and L1OO-55 (soluble at pH 5.5 and above). EUDRAGIT™ 1,100D (soluble at pH 6.0 and above), EUDRAGIT™ S (soluble at pH 7.0 and above, as a result of a higher degree of esterification), and EUDRAGIT™ NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylase and guar gum; zein and shellac. Combinations of different coating, materials may also be used. Multi-layer coatings using different polymers may also be applied. The preferred coating weights for particular coating materials may be readily determined by those skilled in the art by evaluating individual release profiles for tablets, beads and granules prepared with different quantities of various coating materials. It is the combination of materials, method, and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Alternatively, a delayed release tablet may be formulated by dispersing tire drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate, and vinyl or enzymatically degradable polymers or copolymers as described above. These hydrophilic polymers are particularly useful for providing a delayed release matrix. Fatty compounds for use as a matrix material include, but are hot limited to, waxes (e,g. carnauba wax) and glycerol tristearate. Once the active ingredient is mixed with the matrix material, the mixture can be compressed into tablets.

A pulsed release dosage form is one that mimics a multiple dosing profile without repeated dosing and typically allows at least a twofold reduction in dosing frequency as compared to the drug presented as a conventional dosage form (e.g., as a solution or prompt drug-releasing, conventional solid dosage form). A pulsed release profile is characterized by a time period of no release (lag time) or reduced release followed by rapid drug release.

Each dosage form contains a therapeutically effective amount of active agent. In one embodiment of dosage forms that mimic a twice daily dosing profile, approximately 30 wt. % to 70 wt. %, preferably 40 wt. % to 60 wt. %, of the total amount of active agent in the dosage form is released in the initial pulse, and, correspondingly approximately 70 wt. % to 3.0 wt. %, preferably 60 wt. % to 40 wt. %, of the total amount of active agent in the dosage form is released in the second pulse. For dosage forms mimicking the twice daily dosing profile, the second pulse is preferably released approximately 3 hours to less than 14 hours, and more preferably approximately 5 hours to 12 hours, following administration.

For dosage forms mimicking a three times daily dosing profile, approximately 25 wt. % to 40 wt. % of the total amount of active agent in the dosage form is released in the initial pulse, and approximately 25 wt. % to 40 wt. % of the total amount of active agent in the dosage form is released in each of the second and third pulses. For dosage forms that mimic a three times daily dosing profile, release of the second pulse preferably takes place approximately 3 hours to 10 hours, and more preferably approximately 4 to 9 hours, following oral administration. Release of the third pulse occurs about 2 hours to about 8 hours following the second pulse, which is typically about 5 hours to approximately 18 hours following oral administration.

The dosage form can be a closed capsule housing at least two drug-containing dosage units, each dosage unit containing one or more compressed tablets, or may contain, a plurality of beads, granules or particles, providing that each dosage unit has a different drug release profile. The immediate release dosage unit releases drug substantially immediately following oral administration to provide an initial dose. The delayed release dosage unit releases drug approximately 3 hours to 14 hours following oral administration to provide a second dose. Finally, an optional second delayed release dosage unit releases drug about 2 hours to 8 hours following the release of the second dose, which is typically 5 hours to 18 hours following oral administration.

Another dosage form contains a compressed tablet or a capsule having a drug-containing immediate release dosage unit, a delayed release dosage unit and an optional second delayed release dosage unit. In this dosage form, the immediate release dosage unit contains a plurality of beads, granules particles that release drug substantially immediately following oral administration to provide an initial dose. The delayed release dosage unit contains a plurality of coated beads or granules, which release drug approximately 3 hours to 14 hours following oral administration to provide a second dose.

An optional second delayed release dosage unit contains coated beads or granules that release drug about 2 to 8 hours following administration of the initial delayed release dose, which is typically 5 to 18 hours following oral administration. The beads or granules in the delayed release dosage unites) are coated with a bioerodible polymeric material. This coating prevents the drug from being released until the appropriate time, i.e., approximately 3 hours to less than 14 hours following oral administration for the delayed release dosage unit and at least 5 hours to approximately 18 hours following oral administration for the optional second delayed release dosage unit. In this dosage form the components may be admixed in the tablet or may be layered to form a laminated tablet.

Another dosage form is a tablet having a drug-containing immediate release dosage unit, a delayed release dosage unit, and an optional second delayed release dosage unit, wherein the immediate release dosage unit comprises an outer layer that releases the drug substantially immediately following oral administration. The arrangement of the remaining delayed release dosage(s), however, depends upon whether the dosage form is designed to mimic twice daily dosing or three times daily dosing.

In the dosage form mimicking twice daily dosing, the delayed release dosage unit contains an inner core that is coated with a bioerodible polymeric material. The coating is applied such that release of the drug occurs approximately 3 hours to less than 14 hours following oral administration. In this form, the outer layer completely surrounds the inner core. In the dosage form mimicking three times a day dosing, the (first) delayed release dose contains an internal layer that releases drug approximately 3 hours to less than 14 hours following oral administration. This internal layer is surrounded by the outer layer. The second delayed release dosage unit generally contains an inner core that releases the drug at least 5 hours to approximately 18 hours following oral administration. Thus, the layers of this tablet (starting from the external surface) contain an outer layer, an internal layer and an inner core. The inner core contains delayed release beads or granules. Furthermore, the internal layer contains the drug coated with a bioerodible polymeric material. Alternatively, in this particular dosage form mimicking three times a day dosing, both the delayed release dosage unit and second delayed release dosage units are surrounded by an inner layer. This inner layer is free of active agent. Thus, the layers of this tablet (starting from the external surface) comprise an outer layer, inner layer and an admixture of the delayed release dosage units. The first delayed release pulse occurs once the inner layer is substantially eroded thereby releasing the admixture of the delayed release dosage units. The dose corresponding to the (first) delayed release dosage unit is released immediately since the inner layer has prevented access to this dose for the appropriate time, e.g., from approximately 3 hours to 10 hours. The second delayed release dose, however, is formulated to effectively delay release for at least 5 hours to approximately 18 hours following oral administration.

For formulations mimicking twice daily dosing, it is preferred that the delayed release dose is released approximately 3 hours to up to 14 hours, more preferably approximately 5 hours to up to 12 hours, following oral administration. For formulations mimicking three times daily dosing, it is preferred that the (first) delayed release dose is released approximately 3 to 10 hours, preferably 4 hours to 9 hours, following oral administration. For dosage forms containing a third dose, the third dose (i.e., the second delayed release dose) is released at least 5 hours to approximately 18 hours following oral administration.

In still another embodiment, a dosage form is provided which contains a coated core-type delivery system wherein the outer layer contains an immediate release dosage unit containing an active agent, such that the active agent therein is immediately released following oral administration; an intermediate layer there under which surrounds a core; and a core which contains immediate release beads or granules and delayed release beads or granules, such that the second dose is provided by the immediate release beads or granules and the third dose is provided by the delayed release beads or granules.

For purposes of transdermal (e.g., topical) administration, dilute sterile, aqueous or partially aqueous solutions (usually in about 0.1% to 5% concentration), otherwise similar to the above parenteral solutions, may be prepared.

Methods of preparing various pharmaceutical compositions with a certain amount of one or more compounds of formula I or other active agents are known, or will be apparent in light of this disclosure, to those skilled in this art. For examples of methods of preparing pharmaceutical compositions, see Remington's Pharmaceutical Sciences, Mack Publishing Company, Easton, Pa., 19th Edition (1995).

In addition, in certain embodiments, subject compositions of the present application maybe lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject composition which may be combined with a carrier material to produce a single dose may vary depending upon the subject being treated, and the particular mode of administration.

Methods of preparing these formulations or compositions include the step of bringing into association subject compositions with the carrier and, optionally, one or more accessory ingredients. In general, the formulations are prepared by uniformly and intimately bringing into association a subject composition with liquid carriers, or finely divided solid carriers, or both, and then, if necessary, shaping the product.

The compounds of formula I described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may for example contain 0.005-90% w/w, for instance 0.005-50%, 0.005-5% w/w, or 0.01-1.0% w/w, of medicament relative to the total weight of the formulation.

It is desirable, but by no means required, that the formulations herein contain no components which may provoke the degradation of stratospheric ozone. In particular it is desirable that the formulations are substantially free of chlorofluorocarbons such as CC13F, CC12F2 and CF3CC13. As used to refer to ozone-damaging agents, "substantially free" means less than 1% w/w based upon the propellant system, in particular less than 0.5%, for example 0.1% or less.

The propellant may optionally contain an adjuvant having a higher polarity and/or a higher boiling point than the propellant. Polar adjuvants which may be used include (e.g., C2-6) aliphatic alcohols and polyols such as ethanol, isopropanol and propylene glycol. In general, only small quantities of polar adjuvants (e.g., 0.05-3.0% w/w) may be required to improve the stability of the dispersion—the use of quantities in excess of 5% w/w may tend to dissolve the medicament. The formulations described herein may contain less than 1% w/w, e.g., about 0.1% w/w, of polar adjuvant. However, the formulations may be substantially free of polar adjuvants, such as ethanol. Suitable volatile adjuvants include saturated hydrocarbons such as propane, n-butane, isobutane, pentane and isopentane and alkyl ethers such as dimethyl ether. In general, up to 50% w/w of the propellant may comprise a volatile adjuvant, for example 1 to 30% w/w of a volatile saturated C1-C6 hydrocarbon.

Optionally, the aerosol formulations may further comprise one or more surfactants. The surfactants must be physiologically acceptable upon administration by inhalation. Within this category are included surfactants such as L-α-phosphatidylcholine (PC), 1,2-dipalmitoylphosphatidycholine (DPPC), oleic acid, sorbitan trioleate, sorbitan mono-oleate, sorbitan monolaurate, polyoxyethylene (20) sorbitan monolaurate, polyoxyethylene (20) sorbitan monooleate, natural lecithin, oleyl polyoxyethylene (2) ether, stearyl polyoxyethylene (2) ether, lauryl polyoxyethylene (4) ether, block copolymers of oxyethylene and oxypropylene, synthetic lecithin, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol 400, cetyl pyridinium chloride, benzalkonium chloride, olive oil, glyceryl monolaurate, corn oil, cotton seed oil, and sunflower seed oil. Appropriate surfactants include lecithin, oleic acid, and sorbitan trioleate.

Ophthalmic formulations, eye ointments, powders, solutions and the like, are also contemplated as being within the scope of the disclosures herein.

Certain pharmaceutical compositions disclosed herein suitable for parenteral administration comprise one or more subject compositions in combination with one or more pharmaceutically acceptable sterile, isotonic, aqueous, or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition as an active ingredient. Subject compositions may also be administered as a bolus, electuary, or paste.

In solid dosage forms for oral administration (capsules, tablets, pills, dragees, powders, granules and the like), the subject composition is mixed with one or more pharmaceutically acceptable carriers and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using lactose or milk sugars, as well as high molecular weight polyethylene glycols and the like.

A tablet may be made by compression or molding, optionally with one or more accessory ingredients. Compressed tablets may be prepared using a binder (for example, gelatin or hydroxypropylmethyl cellulose), lubricant, inert diluent, preservative, disintegrant (for example, sodium starch glycolate or cross-linked sodium carboxymethyl cellulose), surface-altering or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

There has been widespread use of tablets since the latter part of the 19th century and the majority of pharmaceutical dosage forms are marketed as tablets. Major reasons of tablet popularity as a dosage form are simplicity, low cost and the speed of production. Other reasons include stability of drug product, convenience in packaging, shipping and dispensing. To the patient or consumer, tablets offer convenience of administration, ease of accurate dosage, compactness, portability, blandness of taste, ease of administration and elegant distinctive appearance.

Tablets may be plain, film or sugar coated, bisected, embossed, layered or sustained-release. They can be made in a variety of sizes, shapes and colors. Tablets may be swallowed, chewed or dissolved in the buccal cavity or beneath the tongue. They may be dissolved in water for local or topical application. Sterile tablets are normally used for parenteral solutions and for implantation beneath the skin.

In addition to the active or therapeutic ingredients, tablets may contain a number of inert materials known as excipients. They may be classified according to the role they play in the final tablet. The primary composition may include one or more of a filler, binder, lubricant and glidant. Other excipients which give physical characteristics to the finished tablet are coloring agents, and flavors (especially in the case of chewable tablets). Without excipients most drugs and pharmaceutical ingredients cannot be directly-compressed into tablets. This is primarily due to the poor flow and cohesive properties of most drugs. Typically, excipients are added to a formulation to impart good flow and compression characteristics to the material being compressed. Such properties are imparted through pretreatment steps, such as wet granulation, slugging, spray drying spheronization or crystallization.

Lubricants are typically added to prevent the tableting materials from sticking to punches, minimize friction during tablet compression, and allow for removal of the compressed tablet from the die. Such lubricants are commonly included in the final tablet mix in amounts usually of about 1% by weight.

Other desirable characteristics of excipients include the following: high-compressibility to allow strong tablets to be made at low compression forces; impart cohesive qualities to the powdered material; acceptable rate of disintegration; good flow properties that can improve the flow of other excipients in the formula; and cohesiveness (to prevent tablet from crumbling during processing, shipping and handling).

There are at least three commercially important processes for making compressed tablets: wet granulation, direct compression and dry granulation (slugging or roller compaction). The method of preparation and type of excipients are selected to give the tablet formulation the desired physical characteristics that allow for the rapid compression of the tablets. After compression, the tablets must have a number of additional attributes, such as appearance, hardness, disintegrating ability and an acceptable dissolution profile. Choice of fillers and other excipients will depend on the chemical and physical properties of the drug, behavior of the mixture during processing and the properties of the final tablets. Preformulation studies are done to determine the chemical and physical compatibility of the active component with proposed excipients.

The properties of the drug, its dosage forms and the economics of the operation will determine selection of the best process for tableting. Generally, both wet granulation and direct compression are used in developing a tablet.

One formulation comprises the following: a compound of Formula I, and a binder. Examples of pharmaceutically acceptable binders include, but are not limited to, starches; celluloses and derivatives thereof, e.g., microcrystalline cellulose, hydroxypropyl cellulose hydroxylethyl cellulose and hydroxylpropylmethyl cellulose; sucrose; dextrose; corn syrup; polysaccharides; and gelatin. The binder, e.g., may be present in an amount from about 1% to about 40% by weight of the composition such as 1% to 30% or 1% to 25% or 1% to 20%.

Optionally, one, two, three or more diluents can be added to the formulations disclosed herein. Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 15% to about 40% by weight of the composition. In certain embodiments, diluents are microcrystalline cellulose which is manufactured by the controlled hydrolysis of alpha-cellulose, obtained as a pulp from fibrous plant materials, with dilute mineral acid solutions. Following hydrolysis, the hydrocellulose is purified by filtration and the aqueous slurry is spray dried to form dry, porous particles of a broad size distribution. Suitable microcrystalline cellulose will have an average particle size of from about 20 nm to about 200 nm. Microcrystalline cellulose is available from several suppliers. Suitable microcrystalline cellulose includes Avicel PH 101, Avicel PH 102, Avicel PH 103, Avicel PH 105 and Avicel PH 200, manufactured by FMC Corporation. The microcrystalline cellulose may be present in a tablet formulation in an amount of from about 25% to about 70% by weight. Another appropriate range of this material is from about 30% to about 35% by weight; yet another appropriate range of from about 30% to about 32% by weight. Another diluent is lactose. The lactose may be ground to have an average particle size of between about 50 µm and about 500 µm prior to formulating. The lactose may be present in the tablet formulation in an amount of from about 5% to about 40% by weight, and can be from about 18% to about 35% by weight, for example, can be from about 20% to about 25% by weight.

Optionally one, two, three or more disintegrants can be added to the formulations described herein. Examples of pharmaceutically acceptable disintegrants include, but are not limited to, starches; clays; celluloses; alginates; gums; cross-linked polymers, e.g., cross-linked polyvinyl pyrrolidone, cross-linked calcium carboxymethylcellulose and cross-linked sodium carboxymethylcellulose; soy polysaccharides; and guar gum. The disintegrant, e.g., may be present in an amount from about 2% to about 20%, e.g., from about 5% to about 10%, e.g., about 7% about by weight of the composition. A disintegrant is also an optional but useful component of the tablet formulation. Disintegrants are included to ensure that the tablet has an acceptable rate of disintegration. Typical disintegrants include starch derivatives and salts of carboxymethylcellulose. Sodium starch glycolate is one appropriate disintegrant for this formulation. In certain embodiments, the disintegrant is present in the tablet formulation in an amount of from about 0% to about 10% by weight, and can be from about 1% to about 4% by weight, for instance from about 1.5% to about 2.5% by weight.

Optionally one, two, three or more lubricants can be added to the formulations disclosed herein. Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant, e.g., may be present in an amount from about 0.1% to about 5% by weight of the composition; whereas, the glidant, e.g., may be present in an amount from about 0.1% to about 10% by weight. Lubricants are typically added to prevent the tableting materials from sticking to punches, minimize friction during tablet compression and allow for removal of the compressed tablet from the die. Such lubricants are commonly included in the final tablet mix in amounts usually less than 1% by weight. The lubricant component may be hydrophobic or hydrophilic. Examples of such lubricants include stearic acid, talc and magnesium stearate. Magnesium stearate reduces the friction between the die wall and tablet mix during the compression and ejection of the tablets. It helps prevent adhesion of tablets to the punches and dies. Magnesium stearate also aids in the flow of the powder in the hopper and into the die. It has a particle size range of 450-550 microns and a density range of 1.00-1.80 g/mL It is stable and does not polymerize within the tableting mix. One lubricant, magnesium stearate may also be employed in the formulation. In some aspects, the lubricant is present in the tablet formulation in an amount of from about 0.25% to about 6%; also appropriate is a level of about 0.5% to about 4% by weight; and from about 0.1% to about 2% by weight. Other possible lubricants include talc, polyethylene glycol, silica and hardened vegetable oils. In an optional embodiment, the lubricant is not present in the formulation, but is sprayed onto the dies or the punches rather than being added directly to the formulation.

Examples of useful excipients which can optionally be added to the composition are described in the Handbook of Pharmaceutical Excipients, 3rd edition, Edited by A. H. Kibbe, Published by: American Pharmaceutical Association, Washington D.C., ISBN: 0-917330-96-X, or Handbook of Pharmaceutical Excipients (4th edition), Edited by Raymond C Rowe—Publisher: Science and Practice.

Liquid dosage forms for oral administration include pharmaceutically acceptable emulsions, microemulsions, solutions, suspensions, syrups and elixirs. In addition to the subject compositions, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, corn, peanut, sunflower, soybean, olive, castor, and sesame oils), glycerol, tetrahydrofuryl alcohol, polyethylene glycols and fatty acid esters of sorbitan, and mixtures thereof.

Suspensions, in addition to the subject compositions, may contain suspending agents such as, for example, ethoxylated isostearyl alcohols, polyoxyethylene sorbitol, and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating carriers comprising, for example, cocoa butter, polyethylene glycol, a suppository wax, or a salicylate, and which is solid at room temperature, but liquid at body temperature and, therefore, will melt in the appropriate body cavity and release the encapsulated compound(s) and composition(s). Formulations which are suitable for vaginal administration also include pessaries, tampons, creams, gels, pastes, foams, or spray formulations containing such carriers as are known in the art to be appropriate.

Dosage forms for transdermal administration include powders, sprays, ointments, pastes, creams, lotions, gels, solutions, patches, and inhalants. A subject composition may be mixed under sterile conditions with a pharmaceutically acceptable carrier, and with any preservatives, buffers, or propellants that may be required. For transdermal administration, the complexes may include lipophilic and hydrophilic groups to achieve the desired water solubility and transport properties.

The ointments, pastes, creams and gels may contain, in addition to subject compositions, other carriers, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays may contain, in addition to a subject composition, excipients such as lactose, talc, silicic acid, aluminum hydroxide, calcium silicates and polyamide powder, or mixtures of such substances. Sprays may additionally contain customary propellants, such as chlorofluorohydrocarbons and volatile unsubstituted hydrocarbons, such as butane and propane.

Methods of delivering a composition or compositions via a transdermal patch are known in the art. Exemplary patches and methods of patch delivery are described in U.S. Pat. Nos. 6,974,588, 6,564,093, 6,312,716, 6,440,454, 6,267, 983, 6,239,180, and 6,103,275.

In one embodiment, a transdermal patch may comprise an outer backing foil, a matrix and a protective liner wherein a) the composition or compositions are present in the matrix in a solution (which may be oversaturated), b) the matrix may contain 1 to 5% activated SiO2, and c) the matrix may have a moisture content of less than 0.7%. Moisture-free matrix patches which contain activated silicon dioxide in the matrix show an enhanced drug release into the skin.

In another embodiment, a transdermal patch may comprise: a substrate sheet comprising a composite film formed of a resin composition comprising 100 parts by weight of a polyvinyl chloride-polyurethane composite and 2-10 parts by weight of a styrene-ethylene-butylene-styrene copolymer, a first adhesive layer on the one side of the composite film, and a polyalkylene terephthalate film adhered to the one side of the composite film by means of the first adhesive layer, a primer layer which comprises a saturated polyester resin and is formed on the surface of the polyalkylene terephthalate film; and a second adhesive layer comprising a styrene-diene-styrene block copolymer containing a pharmaceutical agent layered on the primer layer. A method for the manufacture of the above-mentioned substrate sheet comprises preparing the above resin composition molding the resin composition into a composite film by a calendar process, and then adhering a polyalkylene terephthalate film on one side of the composite film by means of an adhesive layer thereby forming the substrate sheet, and forming a primer layer comprising a saturated polyester resin on the outer surface of the polyalkylene terephthalate film.

The pharmaceutical compositions herein can be packaged to produce a "reservoir type" transdermal patch with or without a rate-limiting patch membrane. The size of the patch and or the rate limiting membrane can be chosen to deliver the transdermal flux rates desired. Such a transdermal patch can consist of a polypropylene/polyester impervious backing member heat-sealed to a polypropylene porous/permeable membrane with a reservoir there between. The patch can include a pharmaceutically acceptable adhesive (such as a acrylate, silicone or rubber adhesive) on the membrane layer to adhere the patch to the skin of the host, e.g., a mammal such as a human. A release liner such as a polyester release liner can also be provided to cover the adhesive layer prior to application of the patch to the skin as is conventional in the art. This patch assembly can be packaged in an aluminum foil or other suitable pouch, again as is conventional in the art.

Alternatively, the compositions herein can be formulated into a "matrix-type" transdermal patch. Drug Delivery Systems Characteristics and Biomedical Application, R. L Juliano, ed., Oxford University Press. N.Y. (1980); and Controlled Drug Delivery, Vol. I Basic Concepts, Stephen D. Bruck (1983) describe the theory and application of methods useful for transdermal delivery systems. The drug-matrix could be formed utilizing various polymers, e.g. silicone, polyvinyl alcohol. The "drug matrix" may then be packaged into an appropriate transdermal patch.

Another type of patch comprises incorporating the drug directly in a pharmaceutically acceptable adhesive and laminating the drug-containing adhesive onto a suitable backing member, e.g. a polyester backing membrane. The drug should be present at a concentration which will not affect the adhesive properties, and at the same time deliver the required clinical dose.

Transdermal patches may be passive or active. Passive transdermal drug delivery systems currently available, such as the nicotine, estrogen and nitroglycerine patches, deliver small-molecule drugs. Many of the newly developed proteins and peptide drugs are too large to be delivered through passive transdermal patches and may be delivered using technology such as electrical assist (iontophoresis) for large-molecule drugs.

Iontophoresis is a technique employed for enhancing the flux of ionized substances through membranes by application of electric current. One example of an iontophoretic membrane is given in U.S. Pat. No. 5,080,646 to Theeuwes. The principal mechanisms by which iontophoresis enhances molecular transport across the skin are (a) repelling a charged ion from an electrode of the same charge, (b) electroosmosis, the convective movement of solvent that occurs through a charged pore in response the preferential passage of counter-ions when an electric field is applied or (c) increase skin permeability due to application of electrical current.

In some cases, it may be desirable to administer in the form of a kit, it may comprise a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are widely used for the packaging of pharmaceutical unit dosage forms (tablets, capsules, and the like). Blister packs generally consist of a sheet of relatively stiff material covered with a foil of a plastic material that may be transparent. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. In some embodiments the strength of the sheet is such that the tablets or capsules can be removed from the blister pack by manually applying pressure on the recesses whereby an opening is formed in the sheet at the place of the recess. The tablet or capsule can then be removed via said opening.

Methods and compositions for the treatment of Epilepsy and neurological disorders. Among other things, herein is provided a method of treating Epilepsy and neurological disorders, comprising administering to a patient in need thereof a therapeutically effective amount of compound of Formula I:

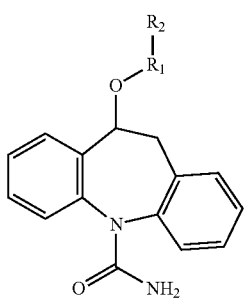
(I)
Wherein,
R[1] independently represents H, D, null,
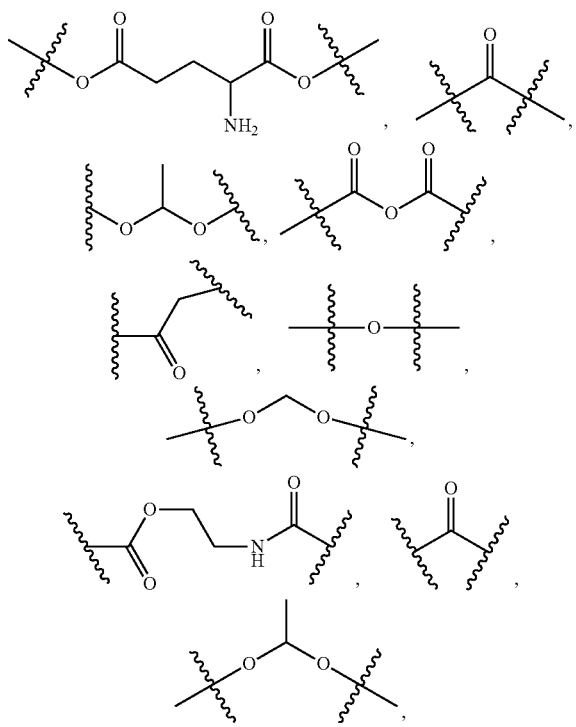
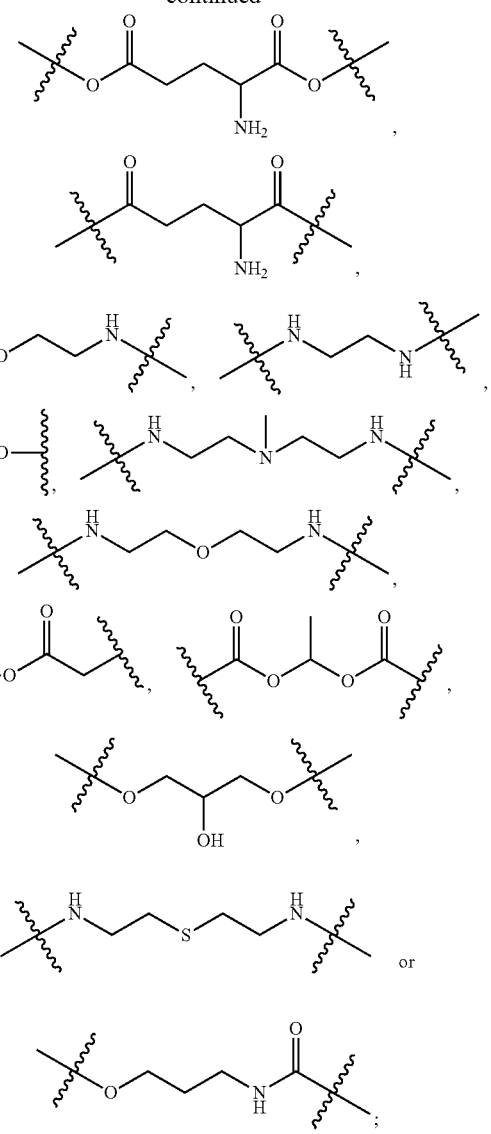
R[2] independently represents
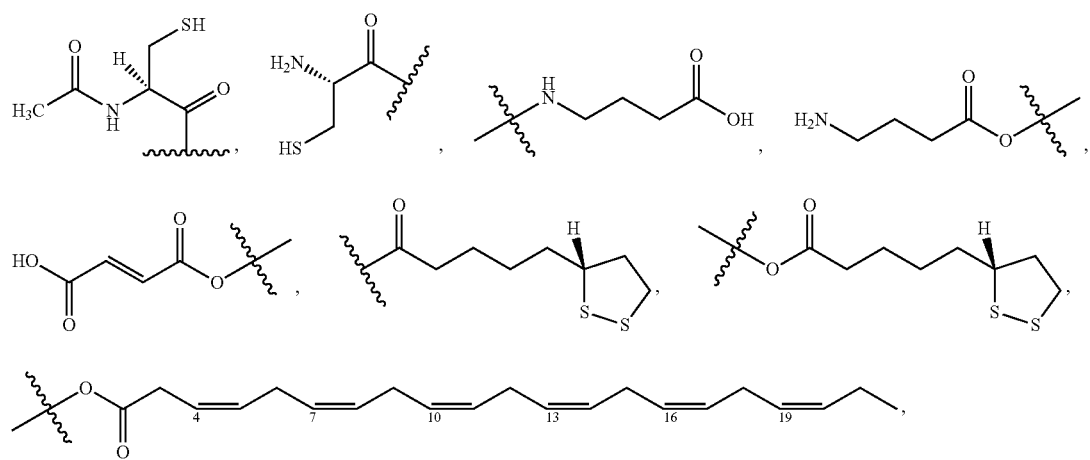

-continued

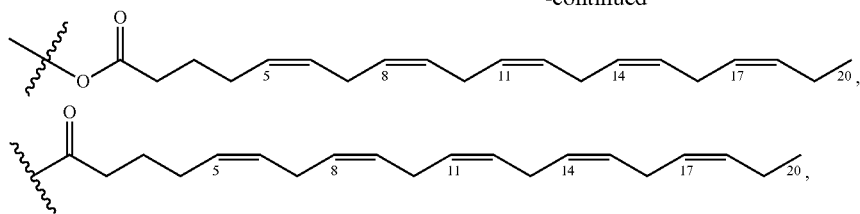

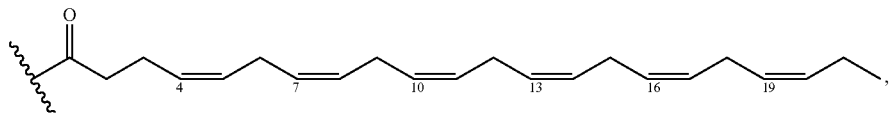

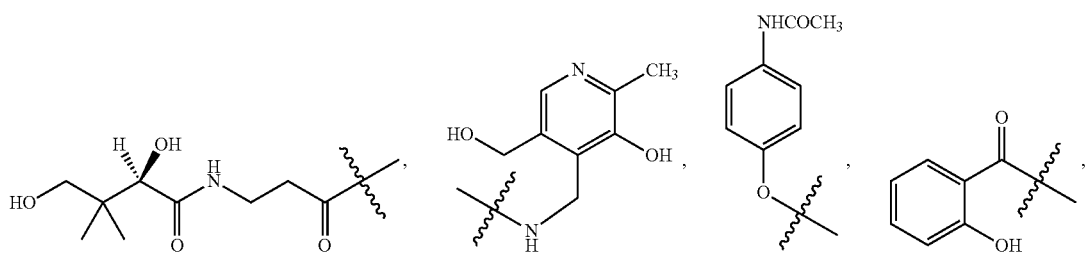

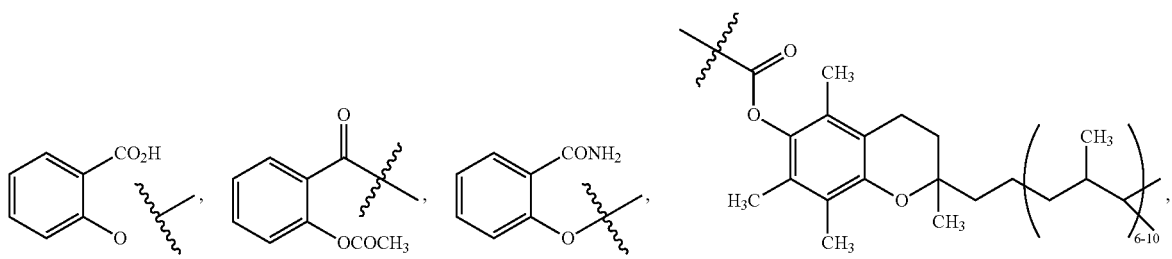

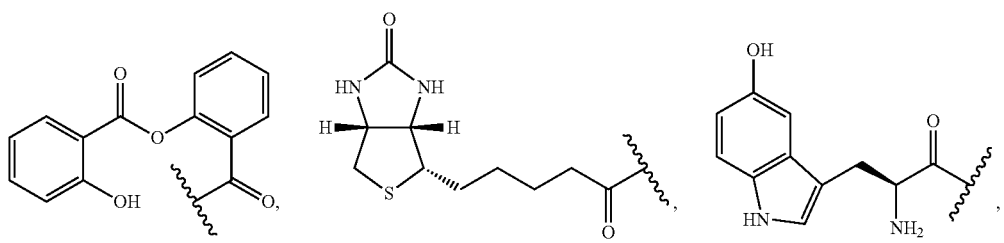

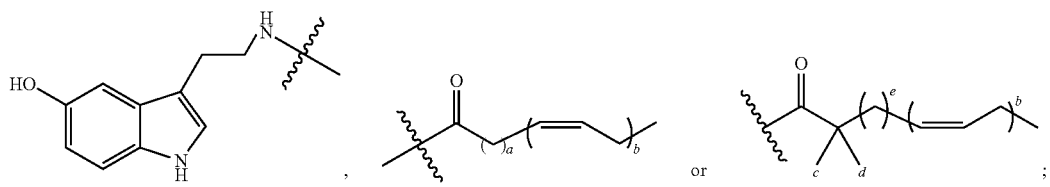

a is independently 2, 3, or 7;
each b is independently 3, 5 or 6;
e is independently 1, 2 or 6;
c and d are each independently H, D, —OH, —OD, $C_1$—$C_6$-alkyl, —$NH_2$ or —$COCH_3$.

Methods and compositions for the treatment of Epilepsy and neurological disorders. Among other things, herein is provided a method of treating Epilepsy and neurological disorders, comprising administering to a patient in need thereof a therapeutically effective amount of compound of biologically active stereoisomer of Formula Ia:

formula Ia
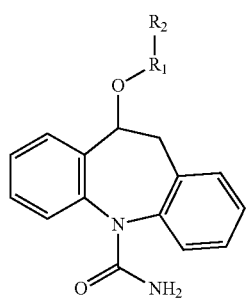
Wherein,
R[1] each independently represents D, NULL,
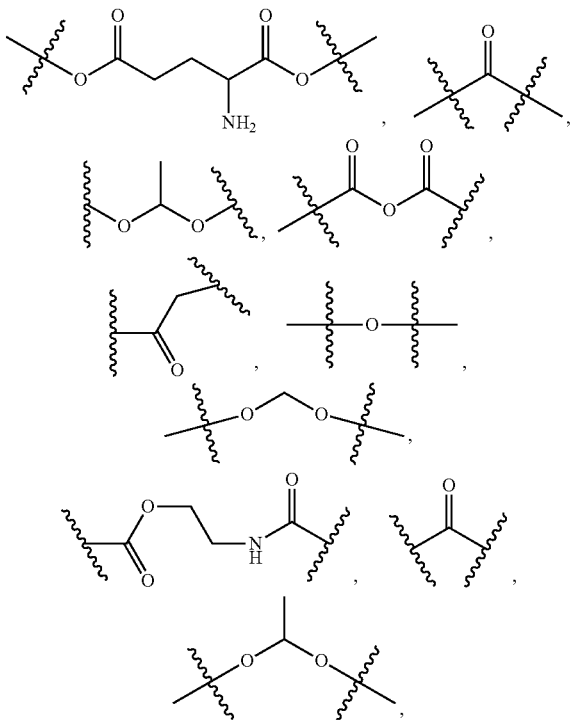
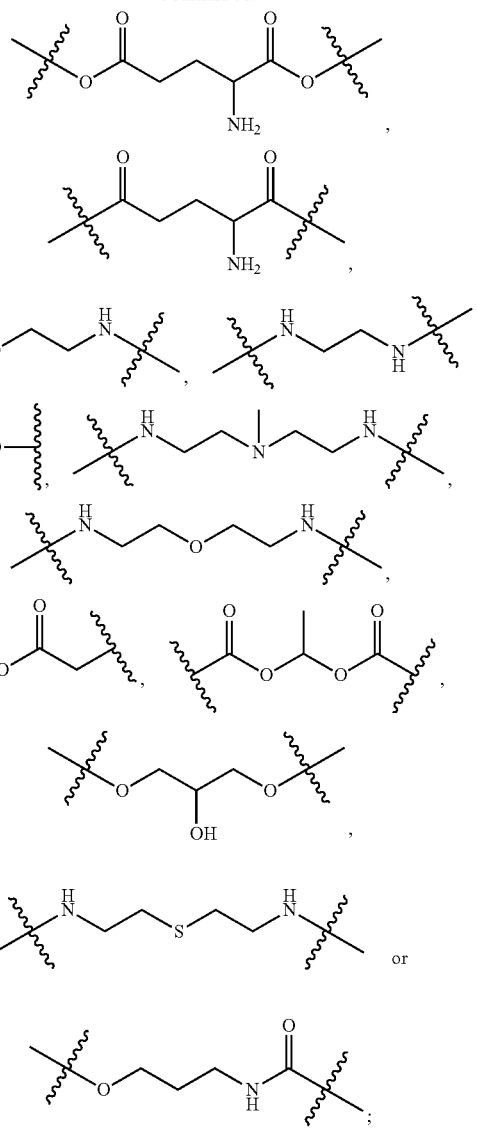
R[2] independently represents
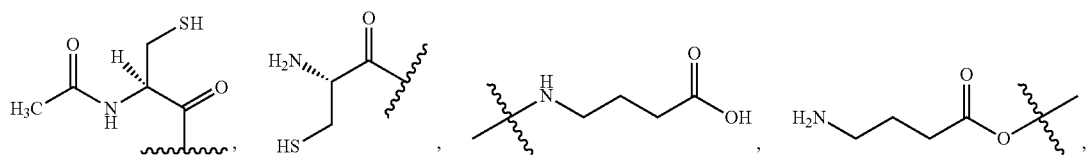
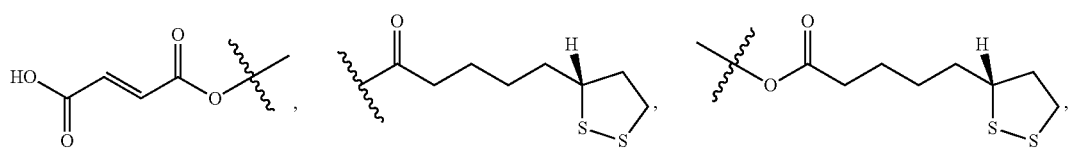
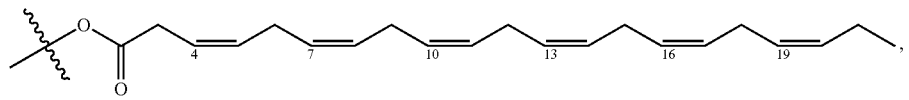

-continued
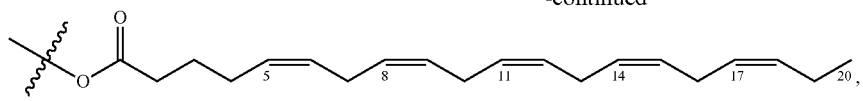
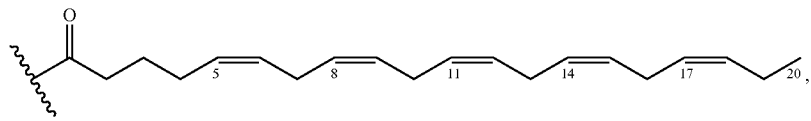
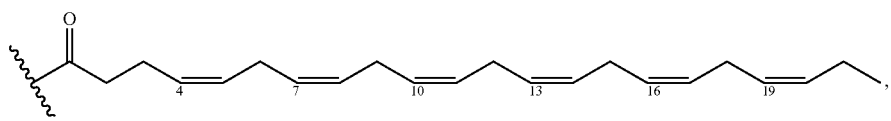
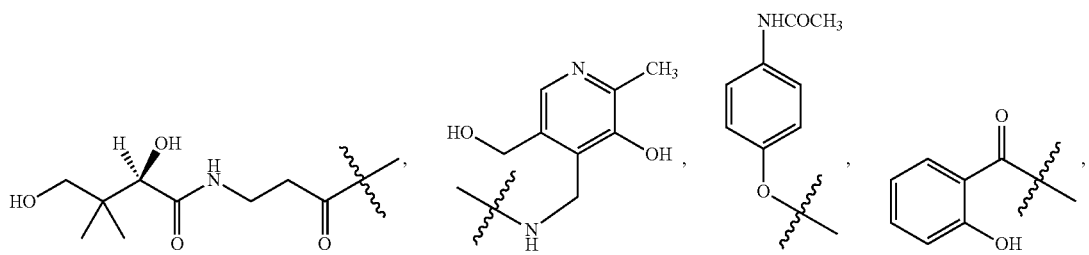
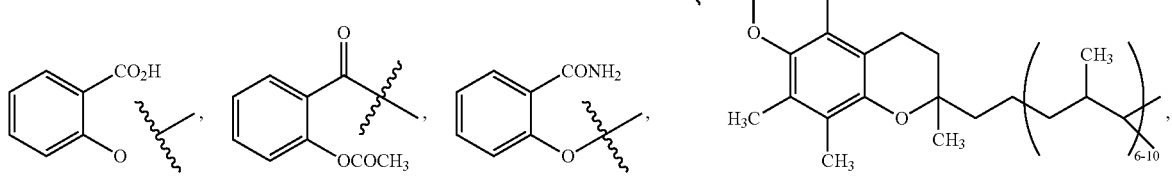
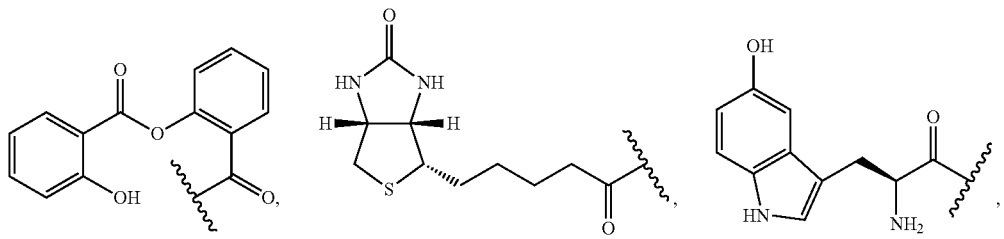
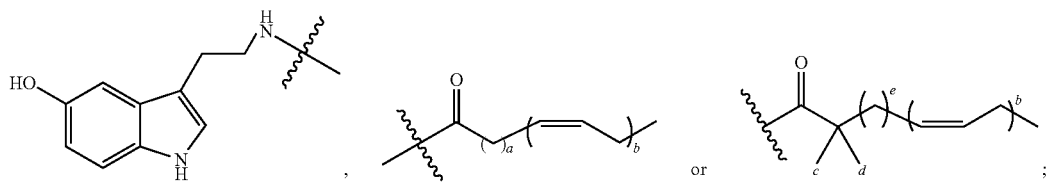
a is independently 2, 3, or 7;
each b is independently 3, 5 or 6;
e is independently 1, 2 or 6;
c and d are each independently H, D, —OH, —OD, $C_1$—$C_6$-alkyl, —$NH_2$ or —$COCH_3$.

Methods of Making

Examples of synthetic pathways useful for making compounds of formula I are set forth in example below and generalized in scheme 1 and scheme 2:

Scheme-1

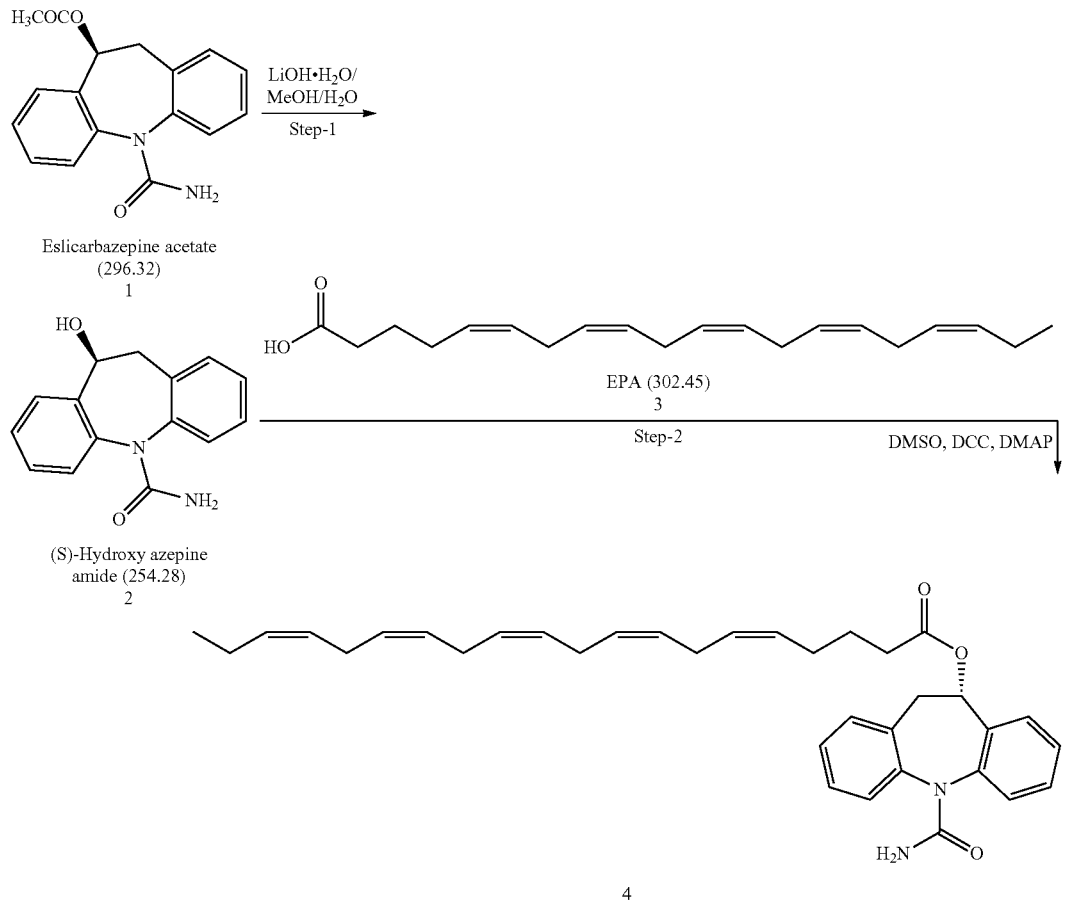

Step-1: Synthesis of Compound 2:

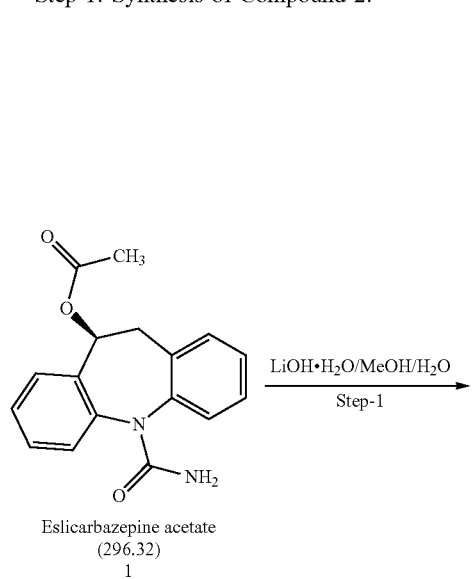

-continued

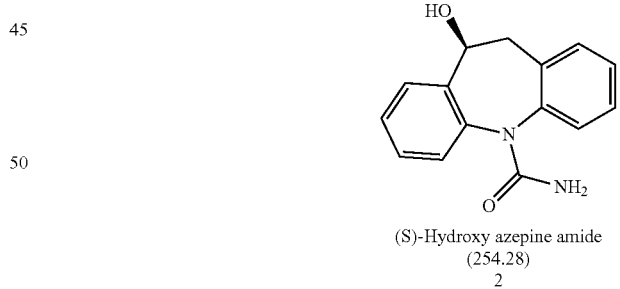

To a solution of Eslicarbazepine acetate (20 g, 0.067 mol) in Methanol (200 ml) was dropwise added the solution of Lithium hydroxide monohydrate (4.24 g, 0.10 mol) in DM water (50 ml) at 10-15° C. Reaction mixture was stirred for 1-2 hrs at 10-15° C. The Progress of reaction was monitored by TLC (5% MeOH in DCM). Reaction mixture was Concentrated under reduced pressure at 40-45° C. DM water (200 ml) was added to residue and stirred the suspension for 1 hr at 0-5° C. White precipitation thus obtained was filtered and washed with Ice-Cold DM water (50 ml), compound 2 was air dried at 45-50° C. till moisture content is achieved NMT 0.5%.

Step-2: Synthesis of Compound 4:

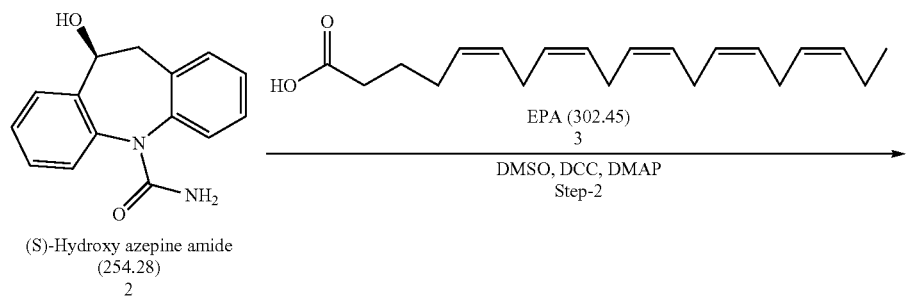

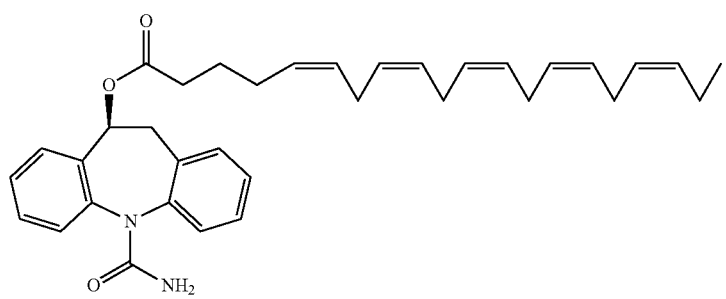

To a solution of compound 2, (S)-Hydroxy azepine amide (5.0 g, 0.0196 mol) in DMSO (25 ml) was added EPA (8.28 g, 0.0274 mol), DMAP (0.5 g, 0.00392 mol) and DCC (6.48 g, 0.0314 mol) at an ambient temperature. Reaction mixture was allowed to stir for 12-15 hrs at an ambient temperature (25-30° C.). Progress of reaction was monitored by TLC (Solvent system: Ethyl acetate). After completion of reaction, DCM (75 ml) and DM water (75 ml) were added to reaction mass followed by layer separation. Aq. layer was re-extracted with DCM (75 ml). Combined DCM layer was washed with 5% Brine solution (75 ml). DCM was distilled off under reduced pressure at 40-45° C. to get crude compound. Crude Compound was further purified by column chromatography (Silica gel; Mesh size-60-120) using 30-50% ethyl acetate in hexane to get pure compound 4 (6 g, 57%) with 98.34% purity by HPLC.

Scheme-2:

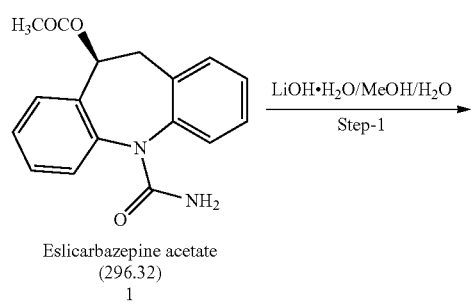

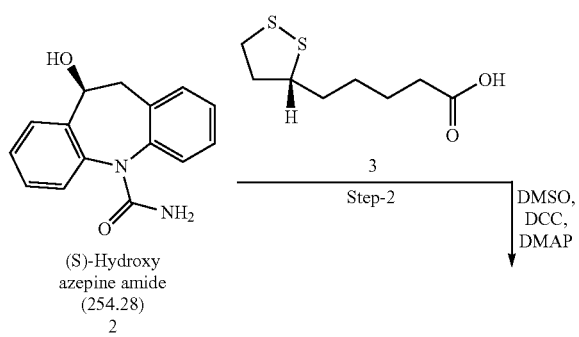

Step-1: Synthesis of Compound 2:

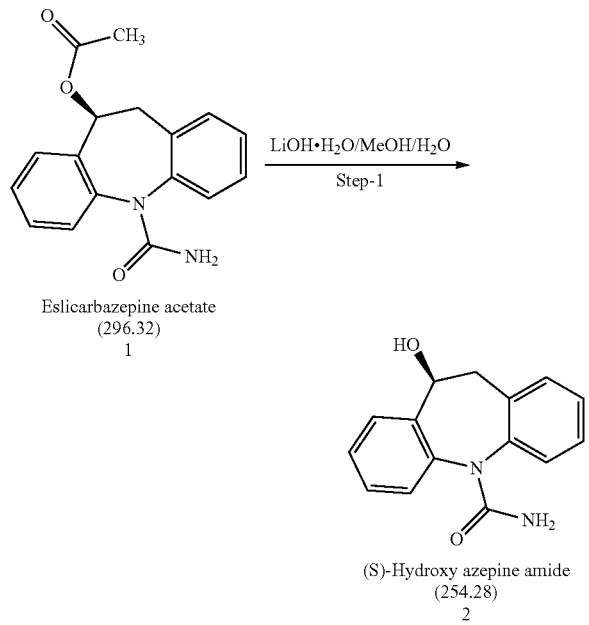

To a solution of Eslicarbazepine acetate (20 g, 0.067 mol) in Methanol (200 ml) was drop wise added the solution of Lithium hydroxide monohydrate (4.24 g, 0.10 mol) in DM water (50 ml) at 10-15° C. Reaction mixture was stirred for 1-2 hrs at 10-15° C. The Progress of reaction was monitored by TLC (5% MeOH in DCM). Reaction mixture was Concentrated under reduced pressure at 40-45° C. DM water (200 ml) was added to residue and stirred the suspension for 1 hr at 0-5° C. White precipitation thus obtained was filtered and washed with Ice-Cold DM water (50 ml), compound 2 was air dried at 45-50° C. till moisture content is achieved NMT 0.5%.

Step-2: Synthesis of Compound 4:

To a solution of compound 2, (S)-Hydroxy azepine amide (5.0 g, 0.0196 mol) in DMSO (25 ml) was added (R)-Lipoic acid (5.65 g, 0.0274 mol), DMAP (0.5 g, 0.0040 mol) and DCC (6.48 g, 0.0314 mol) at an ambient temperature. Reaction mixture was allowed to stir for 12-15 hrs at an ambient temperature (25-30° C.). Progress of reaction was monitored by TLC (Solvent system: Ethyl acetate). After completion of reaction, DCM (75 ml) and DM water (75 ml) were added followed by layer separation. Aq. layer was re-extracted with DCM (75 ml). Combined DCM layer was washed with 5% Brine solution (75 ml). DCM was distilled off under reduced pressure at 40-45° C. to get crude compound. Crude Compound was further purified by column chromatography (Silica gel; Mesh size-60-120) using 30-50% ethyl acetate in hexane to get compound 4 (7.5 g, 74%) with 99.57% purity by HPLC.

EQUIVALENTS

The present disclosure provides among other things compositions and methods for treating Epilepsy and neurological disorders and their complications. While specific embodiments of the subject disclosure have been discussed, the above specification is illustrative and not restrictive. Many variations of the systems and methods herein will become apparent to those skilled in the art upon review of this specification. The full scope of the claimed systems and methods should be determined by reference to the claims, along with their full scope of equivalents, and the specification, along with such variations.

Incorporation by Reference

All publications and patents mentioned herein, including those items listed above, are hereby incorporated by reference in their entirety as if each individual publication or patent was specifically and individually indicated to be incorporated by reference. In case of conflict, the present application, including any definitions herein, will control.

What is claimed is:

1. A compound of Formula I:

or a pharmaceutically acceptable salt thereof, wherein:
$R_1$ independently represents null, 53
-continued
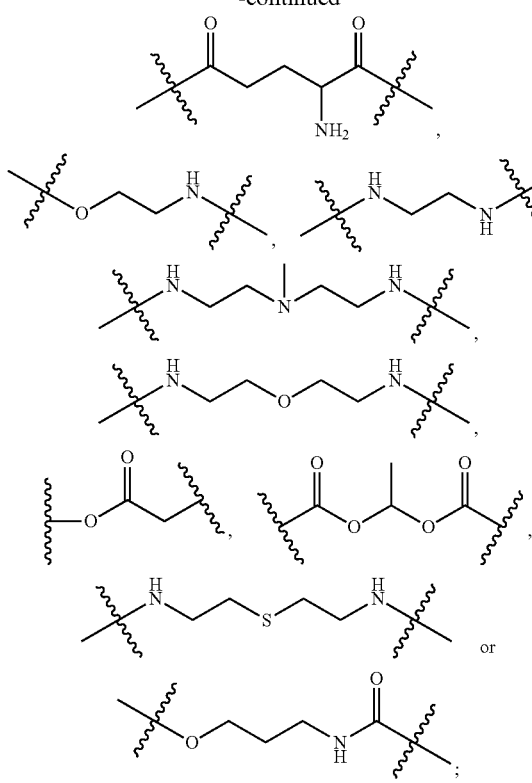
$R_2$ independently represents
54
-continued
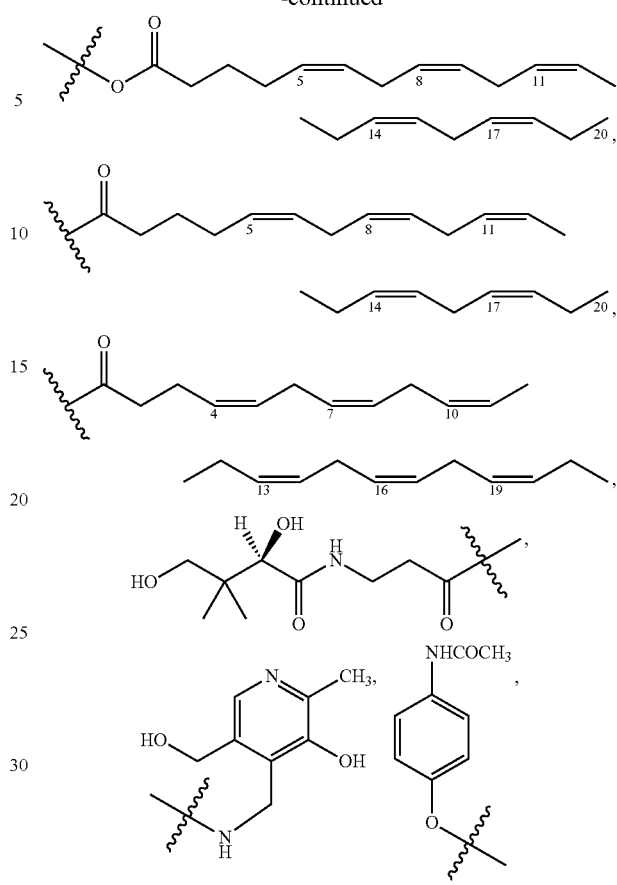
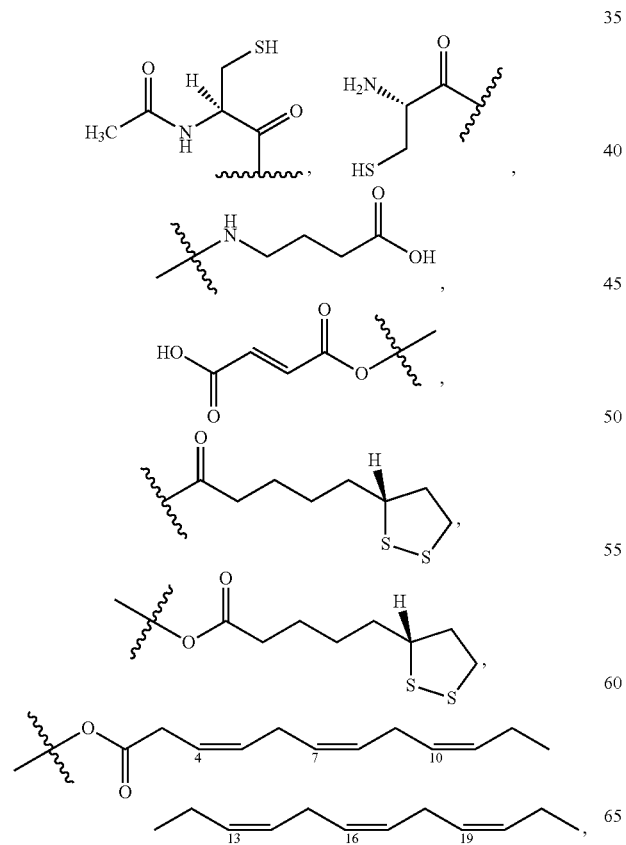

-continued

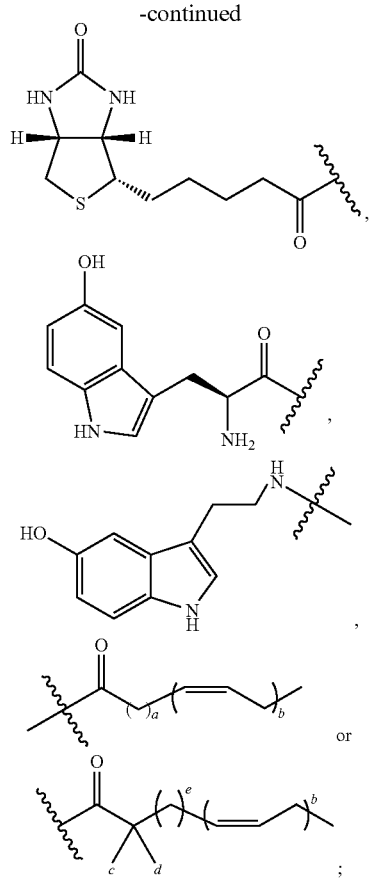

a is independently 2, 3, or 7;
each b is independently 3, 5 or 6;
e is independently 1, 2 or 6;
c and d are each independently H, D, —OH, —OD, $C_1$—$C_6$-alkyl, —$NH_2$ or —$COCH_3$.

2. A compound of Formula Ia, a biologically active stereoisomer or enantiomer of Formula I:

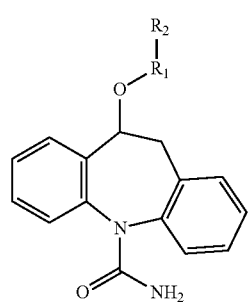

Formula Ia or a pharmaceutically acceptable salt thereof, wherein:

$R_1$ independently represents NULL,

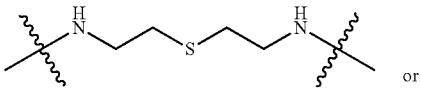

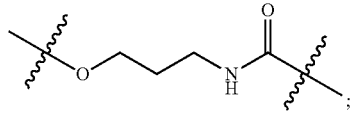

$R_2$ independently represents

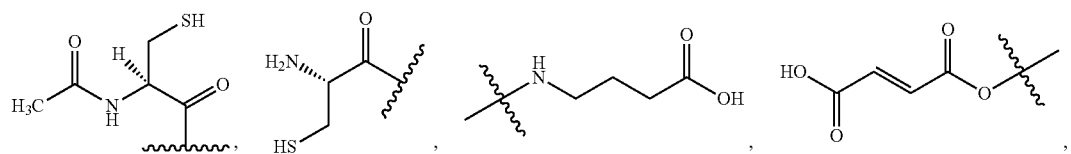

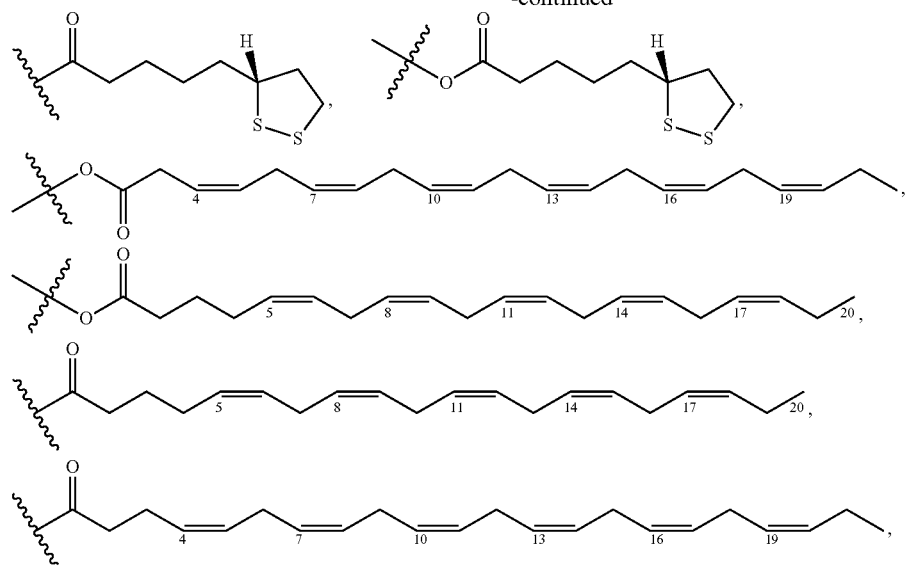
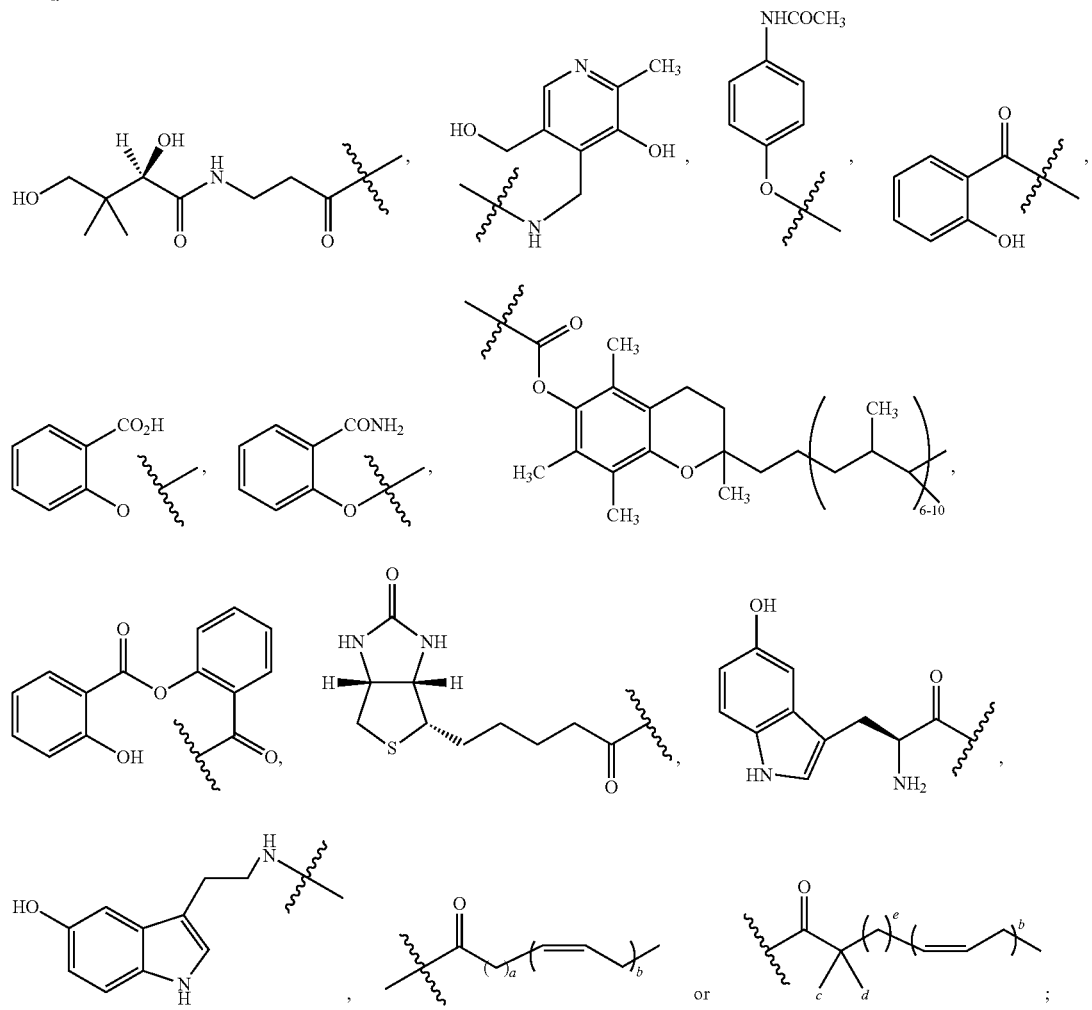
a is independently 2, 3, or 7;
each b is independently 3, 5 or 6;
e is independently 1, 2 or 6;
c and d are each independently H, D, —OH, —OD, $C_1$—$C_6$-alkyl, —$NH_2$ or —$COCH_3$.

3. A pharmaceutical composition comprising a compound of claim 1 and a pharmaceutically acceptable carrier.

4. A pharmaceutical composition comprising a compound of claim 2 and a pharmaceutically acceptable carrier.

5. A compound of claim 1, comprising Formula I:
- (S)-5-carbamoyl-10,11-dihydro-5H-dibenzo[b,f]azepin-10-yl 5-((R)-1,2-dithiolan-3-yl)pentanoate;
- (S)-5-carbamoyl-10,11-dihydro-5H-dibenzo[b,f]azepin-10-yl (5Z,8Z,11Z,14Z,17Z)-icosa-5,8,11,14,17-pentaenoate.

6. A pharmaceutical composition comprising a compound of claim 5 and a pharmaceutically acceptable carrier.

* * * * *